(12) United States Patent
Lilljequist et al.

(10) Patent No.: US 7,459,463 B2
(45) Date of Patent: Dec. 2, 2008

(54) CRYSTALLINE FORMS OF 2,3-DIMETHYL-8-(2,6-DIMETHYLBENZYL-AMINO)-N-HYDROXYETHYL-IMIDAZO[1,2-A] PYRIDINE-6-CARBOXAMIDE MESYLATE SALT

(75) Inventors: Lars Lilljequist, Södertälje (SE); Maria Lindkvist, Mölndal (SE); Peter Nordberg, Möndal (SE); Ursula Pettersson, Södertälje (SE); Tesfai Sebhatu, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/582,838

(22) PCT Filed: Dec. 16, 2004

(86) PCT No.: PCT/SE2004/001909

§ 371 (c)(1),
(2), (4) Date: Jun. 14, 2006

(87) PCT Pub. No.: WO2005/058895

PCT Pub. Date: Jun. 30, 2005

(65) Prior Publication Data

US 2007/0112021 A1  May 17, 2007

(30) Foreign Application Priority Data

Dec. 18, 2003 (SE) .................................. 0303451

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. ..................................... 514/300; 546/121
(58) Field of Classification Search ................. 546/121; 514/300
See application file for complete search history.

(56) References Cited

U.S. PATENT DOCUMENTS

| 5,294,638 | A * | 3/1994 | Hell et al. .................. 514/452 |
| 6,245,818 | B1 | 6/2001 | Lignell et al. |
| 6,313,136 | B1 | 11/2001 | Amin et al. |
| 6,313,137 | B1 | 11/2001 | Amin et al. |
| 2004/0067252 | A1 | 4/2004 | Juppo et al. |
| 2004/0067256 | A1 | 4/2004 | Juppo et al. |

FOREIGN PATENT DOCUMENTS

| WO | 99/55706 | * | 4/1999 |
| WO | WO 99/55705 | | 11/1999 |
| WO | WO 99/55706 | | 11/1999 |
| WO | 02/20523 | * | 3/2002 |
| WO | 02/064118 | * | 8/2002 |
| WO | WO 02/060440 | | 8/2002 |
| WO | WO 02/060441 | | 8/2002 |
| WO | WO 02/060442 | | 8/2002 |
| WO | WO 02/064118 | | 8/2002 |
| WO | 03/094967 | * | 11/2003 |

* cited by examiner

*Primary Examiner*—D. Margaret Seaman
*Assistant Examiner*—Niloofar Rahmani
(74) *Attorney, Agent, or Firm*—White & Case LLP

(57) ABSTRACT

The present invention relates to novel crystalline forms of 2,3-dimethyl-8-(2,6-dimethylbenzylamino)-N-hydroxyethyl-imidazo[1,2-a]pyridine-6-carboxamide mesylate salt and to mixture thereof. Further, the present invention also relates to processes for obtaining them, the use of said compounds for the treatment of gastrointestinal disorders, and pharmaceutical compositions containing them.

28 Claims, 9 Drawing Sheets

An X-ray powder diffractogram of 2,3-dimethyl-8-(2,6-dimethylbenzylamino)-N-hydroxyethyl-imidazo[1,2-a]pyridine-6-carboxamide mesylate salt form A measured with variable slits.

An X-ray powder diffractogram of 2,3-dimethyl-8-(2,6-dimethylbenzylamino)-N-hydroxyethyl-imidazo[1,2-a]pyridine-6-carboxamide mesylate salt form B measured with variable slits.

An X-ray powder diffractogram of 2,3-dimethyl-8-(2,6-dimethylbenzylamino)-N-hydroxyethyl-imidazo[1,2-a]pyridine-6-carboxamide mesylate salt form C measured with variable slits.

An X-ray powder diffractogram of 2,3-dimethyl-8-(2,6-dimethylbenzylamino)-N-hydroxyethyl-imidazo[1,2-a]pyridine-6-carboxamide mesylate salt form E measured An X-ray powder diffractogram of 2,3-dimethyl-8-(2,6-dimethylbenzylamino)-N-hydroxyethyl-imidazo[1,2-a]pyridine-6-carboxamide mesylate salt form G measured with variable slits.

A Raman spectrum of 2,3-dimethyl-8-(2,6-dimethylbenzylamino)-N-hydroxyethyl-imidazo[1,2-a]pyridine-6-carboxamide mesylate salt form A A Raman spectrum of 2,3-dimethyl-8-(2,6-dimethylbenzylamino)-N-hydroxyethyl-imidazo[1,2-a]pyridine-6-carboxamide mesylate salt form B

US 7,459,463 B2

CRYSTALLINE FORMS OF 2,3-DIMETHYL-8-(2,6-DIMETHYLBENZYL-AMINO)-N-HYDROXYETHYL-IMIDAZO[1,2-A]PYRIDINE-6-CARBOXAMIDE MESYLATE SALT

FIELD OF THE INVENTION

The present invention relates to 2,3-dimethyl-8-(2,6-dimethylbenzylamino)-N-hydroxyethyl-imidazo[1,2-a]pyridine-6-carboxamide mesylate salt and novel crystalline forms thereof. Further, the present invention also relates to use of said compounds for the treatment of gastrointestinal disorders, pharmaceutical compositions containing them and processes for obtaining them.

BACKGROUND OF THE INVENTION AND PRIOR ART

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations comprising the active compound.

Further, in the manufacture of oral drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should be capable of being effectively stored over appreciable periods of time, without exhibiting a significant change in the physico-chemical characteristics of the active component, e.g. its chemical composition, density, hygroscopicity and solubility.

Amorphous materials may present problems in this regard. For example, such materials are typically more difficult to handle and to formulate, provide for unreliable solubility, and are often found to be more unstable.

Thus, in the manufacture of commercially viable and pharmaceutically acceptable drug compositions, it is important, wherever possible, to provide the drug in a substantially crystalline and stable form(s).

International patent applications WO 99/55705 and WO 99/55706 disclose a number of compounds, referred to as imidazo pyridine derivatives, which are potassium-competitive blockers of acid secretion, P-CABs, see also N. Vakil, Alimentary Pharmacology & Therapeutics, Volume 19, Issue 10, Page 1041, May 2004.

DESCRIPTION OF THE INVENTION

It has surprisingly been found that 2,3-dimethyl-8-(2,6-dimethylbenzylamino)-N-hydroxyethyl-imidazo[1,2-a]pyridine-6-carboxamide mesylate salt can exist in more than one crystal form. The crystal forms are hereinafter referred to as 2,3-dimethyl-8-(2,6-dimethylbenzylamino)-N-hydroxyethyl-imidazo[1,2-a]pyridine-6-carboxamide mesylate salt form A, form B, form C, form D, form E, form F, form G and form H and also to as the crystal forms of the invention. The notation A, B, C, D, E, F, G and H relates to the order in time in which the forms were invented, not to their relative thermodynamic stability.

The different crystal forms may hereinafter be denoted as form A, form B, form C, form D, form E, form F, form G and form H. It shall be understood that this means the different crystal forms A to H of 2,3-dimethyl-8-(2,6-dimethylbenzylamino)-N-hydroxyethyl-imidazo[1,2-a]pyridine-6-carboxamide mesylate salt, and shall facilitate reading and avoid typographical errors.

It is thus an object of the present invention to provide crystalline forms of 2,3-dimethyl-8-(2,6-dimethylbenzylamino)-N-hydroxyethyl-imidazo[1,2-a]pyridine-6-carboxamide mesylate salt with different advantageous properties and/or effects.

It is an aspect of the present invention to provide 2,3-dimethyl-8-(2,6-dimethylbenzylamino)-N-hydroxyethyl-imidazo[1,2-a]pyridine-6-carboxamide mesylate salt form A.

Figure 1:
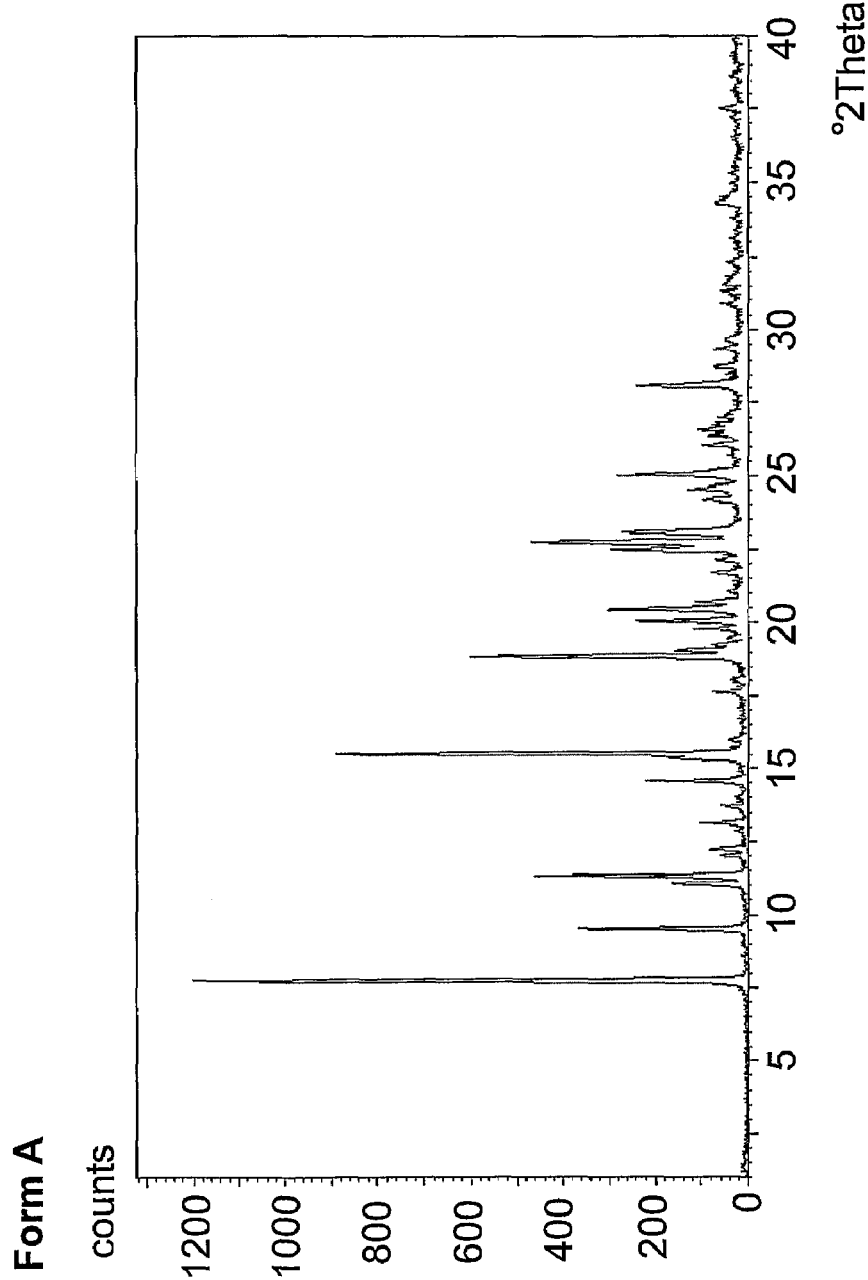
FIG. 1 is an X-ray powder diffractogram of 2,3-dimethyl-8-(2,6-dimethylbenzylamino)-N-hydroxyethyl-imidazo[1,2-a]pyridine-6-carboxamide mesylate salt form A.

2,3-dimethyl-8-(2,6-dimethylbenzylamino)-N-hydroxyethyl-imidazo[1,2-a]pyridine-6-carboxamide mesylate salt form A, according to the present invention, is characterized in providing an X-ray powder diffraction pattern, as in FIG. 1, exhibiting substantially the following d-values:

| Form A d-value (Å) |
| --- |
| 11.4 |
| 9.3 |
| 7.8 |
| 5.7 |
| 4.72 |
| 4.35 |
| 3.92 |
| 3.18 |

2,3-dimethyl-8-(2,6-dimethylbenzylamino)-N-hydroxyethyl-imidazo[1,2-a]pyridine-6-carboxamide mesylate salt form A according to the present invention is further characterized by a monoclinic unit cell with parameters:

$a=8.6$ Å, $b=18.7$ Å, $c=15.8$ Å, $\alpha=90°$, $\beta=113°$, $\gamma=90°$.

Figure 8:
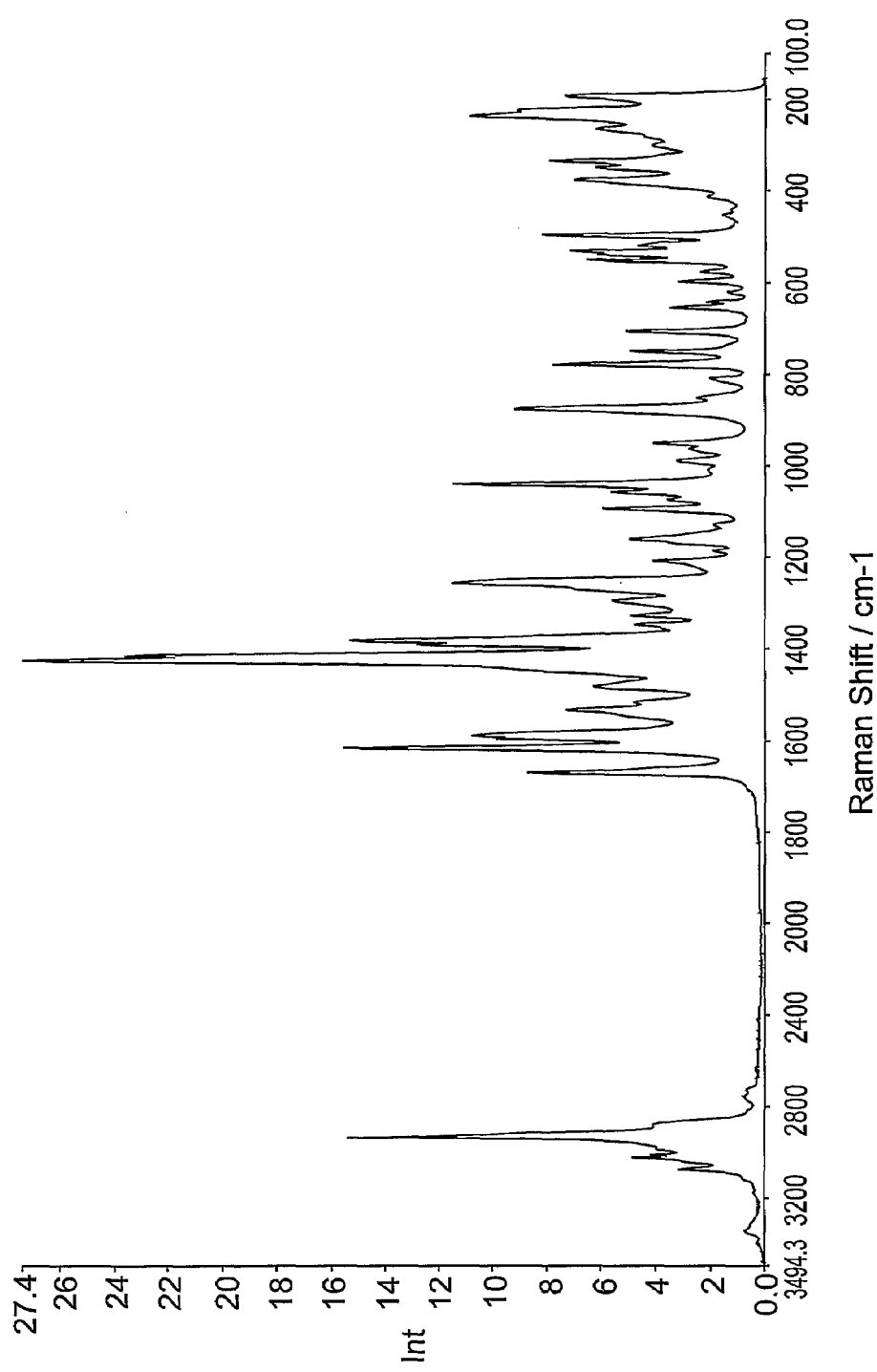
FIG. 8 is a Raman spectrum of 2,3-dimethyl-8-(2,6-dimethylbenzylamino)-N-hydroxyethyl-imidazo[1,2-a]pyridine-6-carboxamide mesylate salt form A.

2,3-dimethyl-8-(2,6-dimethylbenzylamino)-N-hydroxyethyl-imidazo[1,2-a]pyridine-6-carboxamide mesylate salt form A, according to the present invention, is characterized in providing a Raman spectrum as in FIG. 8. Peaks from the spectrum with relative intensities above 18.6 are observed for the following Raman shifts (cm$^{-1}$):

| Raman shift (cm$^{-1}$) | Relative intensity |
| --- | --- |
| 2935.9 | 56.2 |
| 1671.2 | 31.8 |
| 1617.7 | 56.6 |
| 1597.2 | 35.8 |
| 1590.4 | 39.4 |
| 1533.9 | 26.3 |
| 1484.4 | 22.6 |
| 1427.1 | 100.0 |
| 1415.8 | 85.8 |
| 1392.9 | 46.7 |
| 1383.1 | 55.8 |
| 1296.2 | 20.1 |
| 1271.1 | 25.5 |
| 1258.2 | 42.0 |
| 1095.5 | 21.5 |
| 1059.7 | 20.4 |
| 1042.3 | 41.6 |
| 877.6 | 33.6 |
| 781.7 | 28.1 |
| 708.6 | 18.6 |
| 554.9 | 23.7 |
| 542.8 | 22.3 |
| 535.7 | 25.9 |
| 501.2 | 29.9 |
| 379.6 | 25.2 |
| 352.9 | 22.6 |
| 338.1 | 28.8 |
| 268.3 | 22.3 |
| 239.7 | 39.8 |
| 228.2 | 33.2 |
| 196.8 | 26.6 |

It is a further aspect of the present invention to provide 2,3-dimethyl-8-(2,6-dimethylbenzylamino)-N-hydroxyethyl-imidazo[1,2-a]pyridine-6-carboxamide mesylate salt form B.

Figure 2:
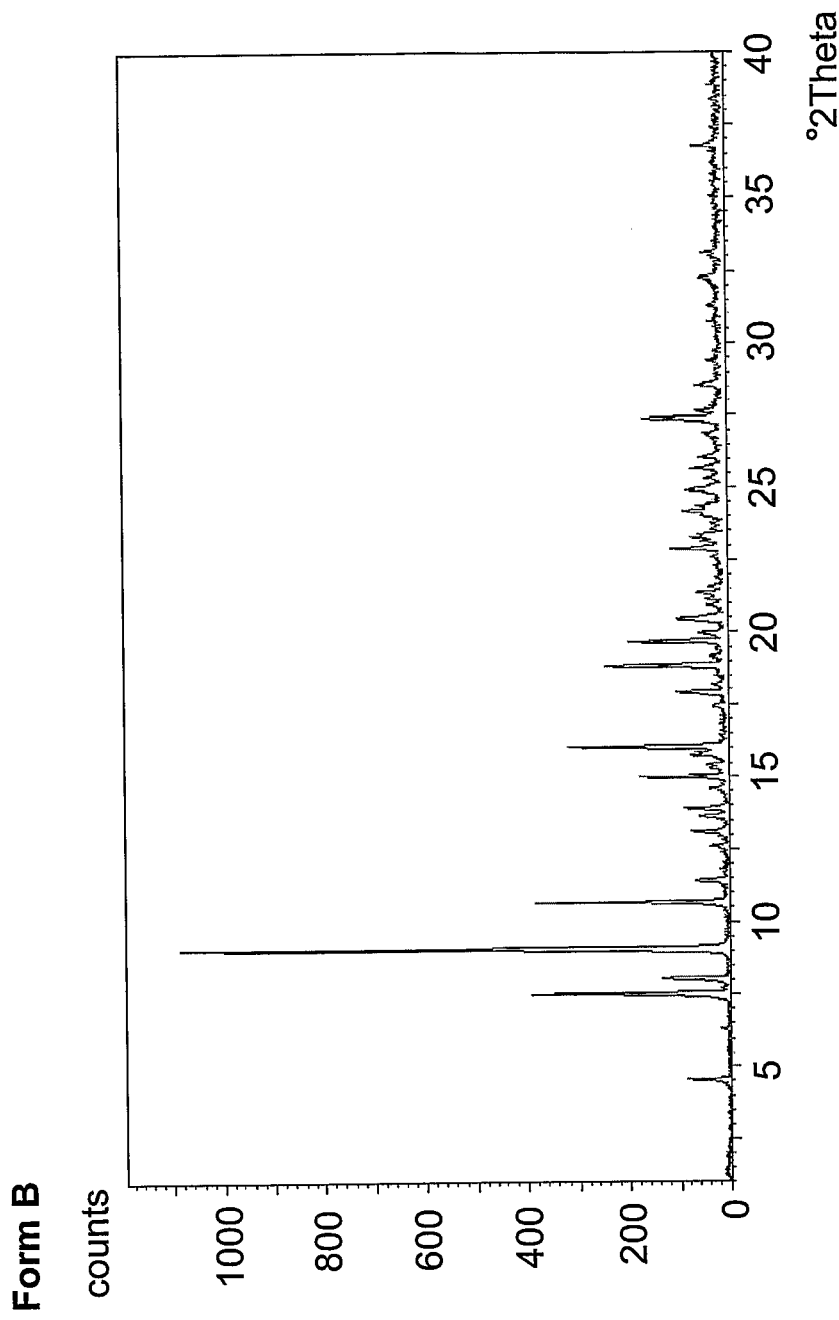
FIG. 2 is an X-ray powder diffractogram of 2,3-dimethyl-8-(2,6-dimethylbenzylamino)-N-hydroxyethyl-imidazo[1,2-a]pyridine-6-carboxamide mesylate salt form B.

2,3-dimethyl-8-(2,6-dimethylbenzylamino)-N-hydroxyethyl-imidazo[1,2-a]pyridine-6-carboxamide mesylate salt form B, according to the present invention, is characterized in providing an X-ray powder diffraction pattern, as in FIG. 2, exhibiting substantially the following d-values:

| Form B d-value (Å) |
| --- |
| 11.8 |
| 11.1 |
| 9.8 |
| 8.3 |
| 5.9 |
| 5.5 |
| 4.72 |
| 4.52 |

2,3-dimethyl-8-(2,6-dimethylbenzylamino)-N-hydroxyethyl-imidazo[1,2-a]pyridine-6-carboxamide mesylate salt form B according to the present invention is further characterized by a triclinic unit cell with parameters:

a=8.4 Å, b=14.2 Å, c=19.9 Å, α=93°, β=100°, γ=97°.

Figure 9:
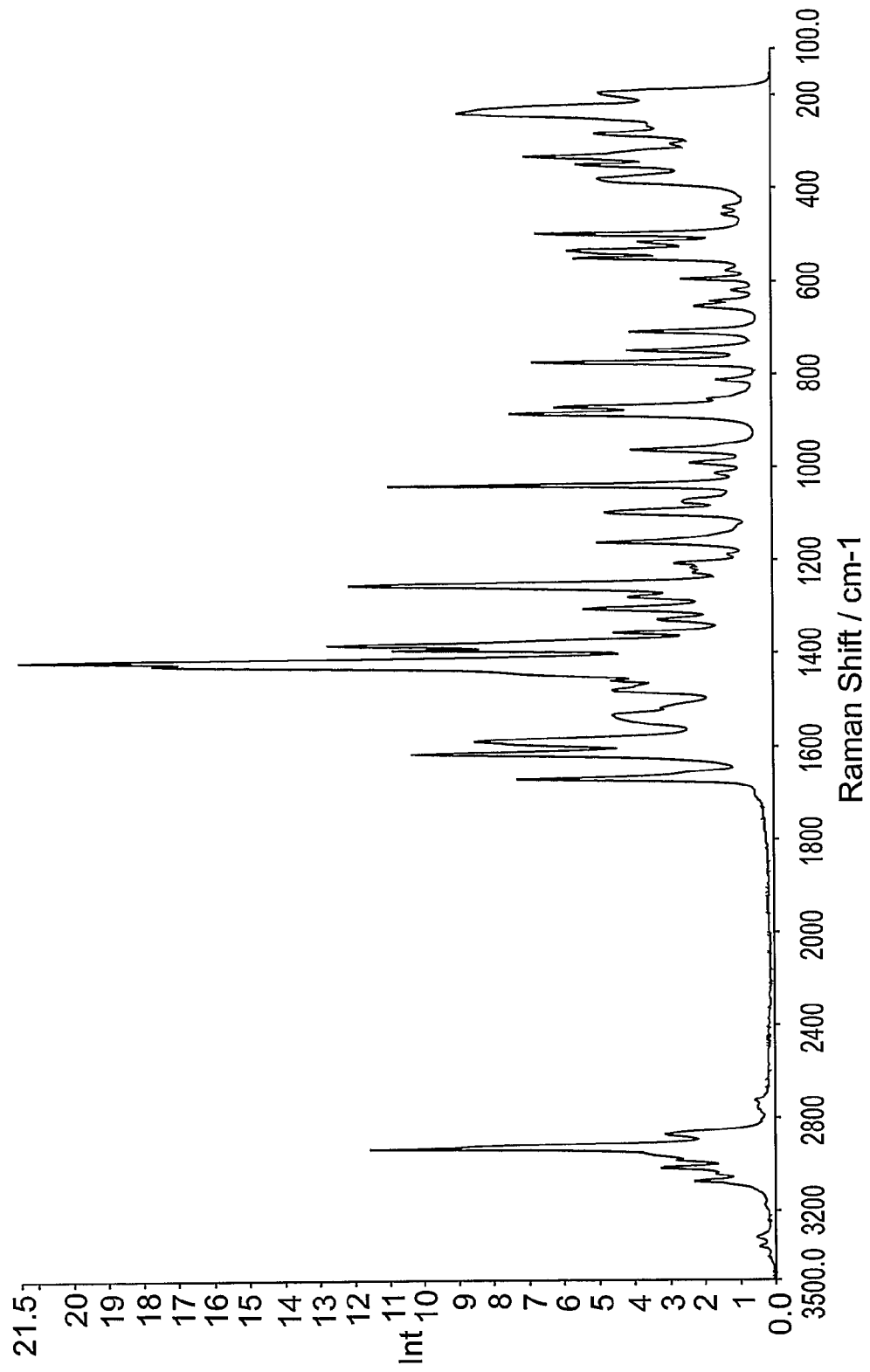
FIG. 9 is a Raman spectrum of 2,3-dimethyl-8-(2,6-dimethylbenzylamino)-N-hydroxyethyl-imidazo[1,2-a]pyridine-6-carboxamide mesylate salt form B.

2,3-dimethyl-8-(2,6-dimethylbenzylamino)-N-hydroxyethyl-imidazo[1,2-a]pyridine-6-carboxamide mesylate salt form B, according to the present invention, is characterized in providing a Raman spectrum as in FIG. 9. Peaks from the spectrum with relative intensities above 18.6 are observed for the following Raman shifts (cm$^{-1}$):

| Raman shift (cm$^{-1}$) | Relative intensity |
| --- | --- |
| 2937.4 | 53.5 |
| 2928.8 | 41.9 |
| 1671.4 | 33.5 |
| 1617.0 | 47.9 |
| 1590.3 | 39.1 |
| 1533.8 | 20.9 |
| 1480.7 | 20.9 |
| 1461.0 | 21.4 |
| 1426.4 | 81.9 |
| 1417.3 | 100.0 |
| 1394.4 | 50.2 |
| 1383.1 | 59.1 |
| 1357.5 | 20.9 |
| 1305.8 | 24.7 |
| 1280.3 | 19.1 |
| 1254.9 | 55.8 |
| 1163.5 | 22.8 |
| 1100.1 | 21.9 |
| 1040.8 | 50.7 |
| 964.9 | 18.6 |
| 888.2 | 34.4 |
| 871.9 | 28.4 |
| 777.4 | 31.6 |
| 751.4 | 19.1 |
| 710.3 | 18.6 |
| 553.1 | 26.0 |
| 536.1 | 26.5 |
| 501.3 | 31.2 |
| 382.3 | 22.3 |
| 353.1 | 25.6 |
| 335.5 | 32.1 |
| 285.4 | 22.8 |
| 241.1 | 41.4 |
| 198.9 | 22.3 |

It is a further aspect of the present invention to provide 2,3-dimethyl-8-(2,6-dimethylbenzylamino)-N-hydroxyethyl-imidazo[1,2-a]pyridine-6-carboxamide mesylate salt form C.

Figure 3:
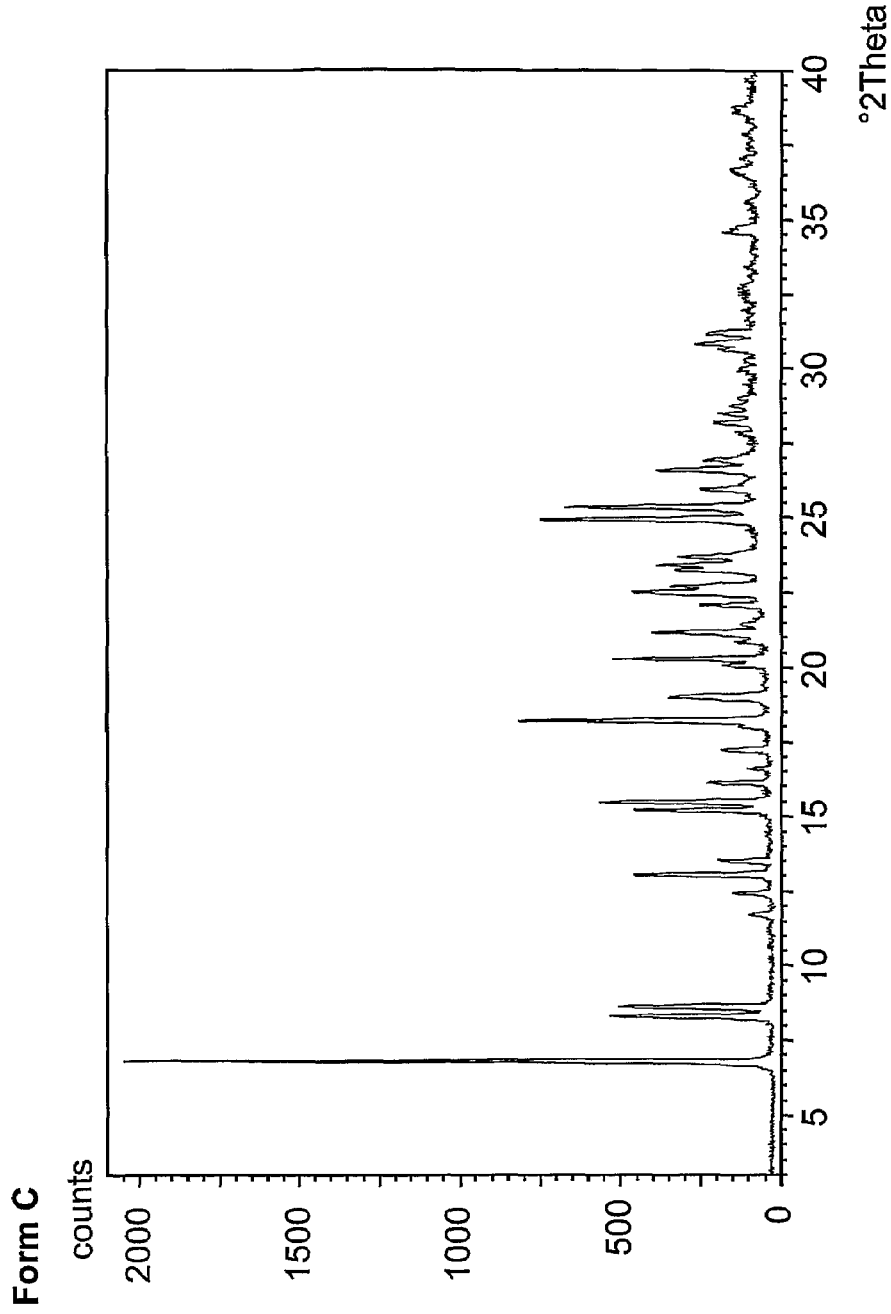
FIG. 3 is an X-ray powder diffractogram of 2,3-dimethyl-8-(2,6-dimethylbenzylamino)-N-hydroxyethyl-imidazo[1,2-a]pyridine-6-carboxamide mesylate salt form C.

2,3-dimethyl-8-(2,6-dimethylbenzylamino)-N-hydroxyethyl-imidazo[1,2-a]pyridine-6-carboxamide mesylate salt form C, according to the present invention, is characterized in providing an X-ray powder diffraction pattern, as in FIG. 3, exhibiting substantially the following d-values:

| Form C d-value (Å) |
| --- |
| 13.1 |
| 10.7 |
| 6.8 |
| 5.7 |
| 4.88 |
| 4.39 |
| 3.57 |
| 3.51 |

It is a further aspect of the present invention to provide 2,3-dimethyl-8-(2,6-dimethylbenzylamino)-N-hydroxyethyl-imidazo[1,2-a]pyridine-6-carboxamide mesylate salt form D.

2,3-dimethyl-8-(2,6-dimethylbenzylamino)-N-hydroxyethyl-imidazo[1,2-a]pyridine-6-carboxamide mesylate salt form D, according to the present invention, is characterized in providing an X-ray powder diffraction pattern exhibiting substantially the following d-values:

| Form D d-value (Å) |
|---|
| 13.8 |
| 9.1 |
| 6.9 |
| 6.4 |
| 5.1 |
| 4.62 |
| 3.55 |
| 2.38 |

2,3-dimethyl-8-(2,6-dimethylbenzylamino)-N-hydroxyethyl-imidazo[1,2-a]pyridine-6-carboxamide mesylate salt form D according to the present invention is further characterized by a triclinic unit cell with parameters:

$a=8.6$ Å, $b=15.9$ Å, $c=19.4$ Å, $\alpha=70°$, $\beta=89°$, $\gamma=75°$.

It is a further aspect of the present invention to provide 2,3-dimethyl-8-(2,6-dimethylbenzylamino)-N-hydroxyethyl-imidazo[1,2-a]pyridine-6-carboxamide mesylate salt form E.

Figure 4:
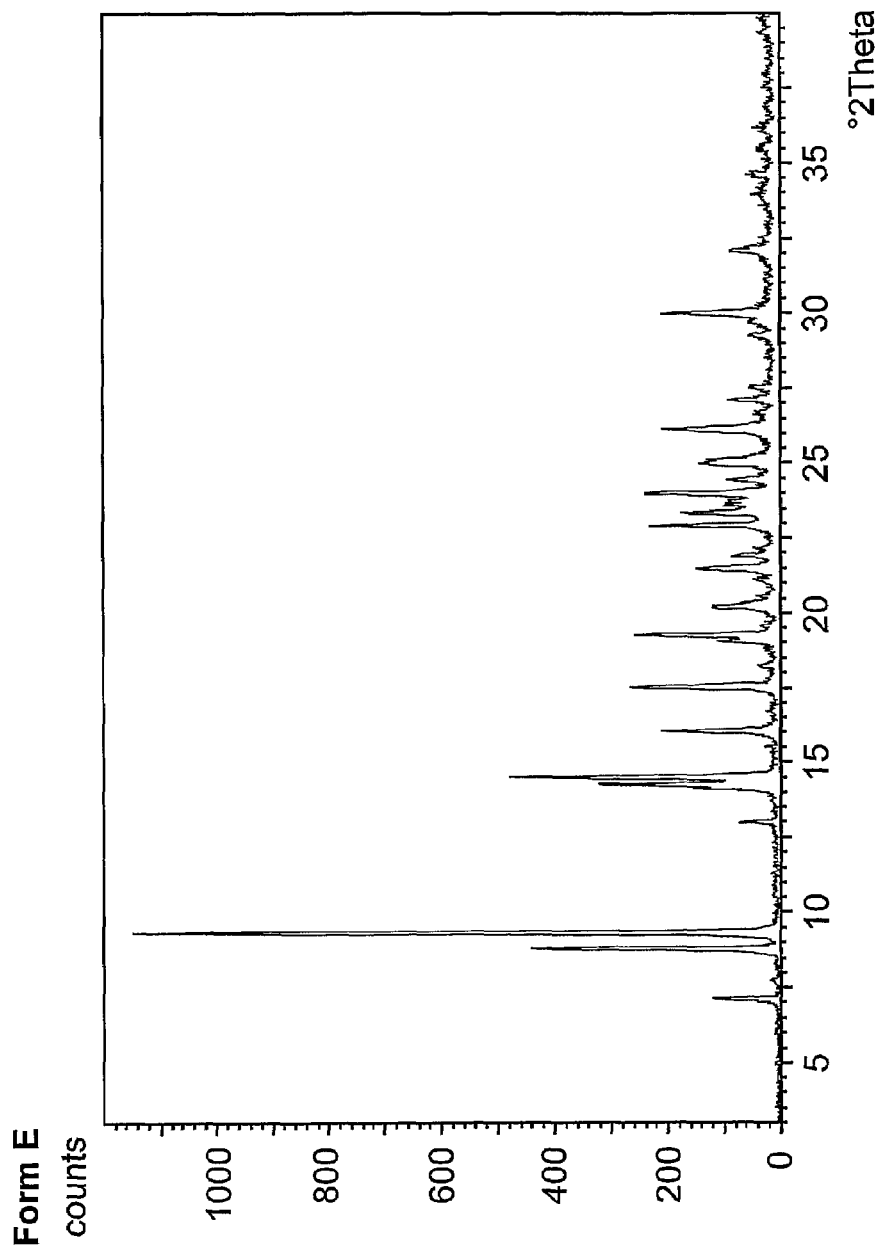
FIG. 4 is an X-ray powder diffractogram of 2,3-dimethyl-8-(2,6-dimethylbenzylamino)-N-hydroxyethyl-imidazo[1,2-a]pyridine-6-carboxamide mesylate salt form E.

2,3-dimethyl-8-(2,6-dimethylbenzylamino)-N-hydroxyethyl-imidazo[1,2-a]pyridine-6-carboxamide mesylate salt form E, according to the present invention, is characterized in providing an X-ray powder diffraction pattern, as in FIG. 4, exhibiting substantially the following d-values:

| Form E d-value (Å) |
|---|
| 12.5 |
| 10.1 |
| 9.5 |
| 6.1 |
| 5.1 |
| 4.61 |
| 3.88 |
| 3.71 |

It is a further aspect of the present invention to provide 2,3-dimethyl-8-(2,6-dimethylbenzylamino)-N-hydroxyethyl-imidazo[1,2-a]pyridine-6-carboxamide mesylate salt form F.

Figure 5:
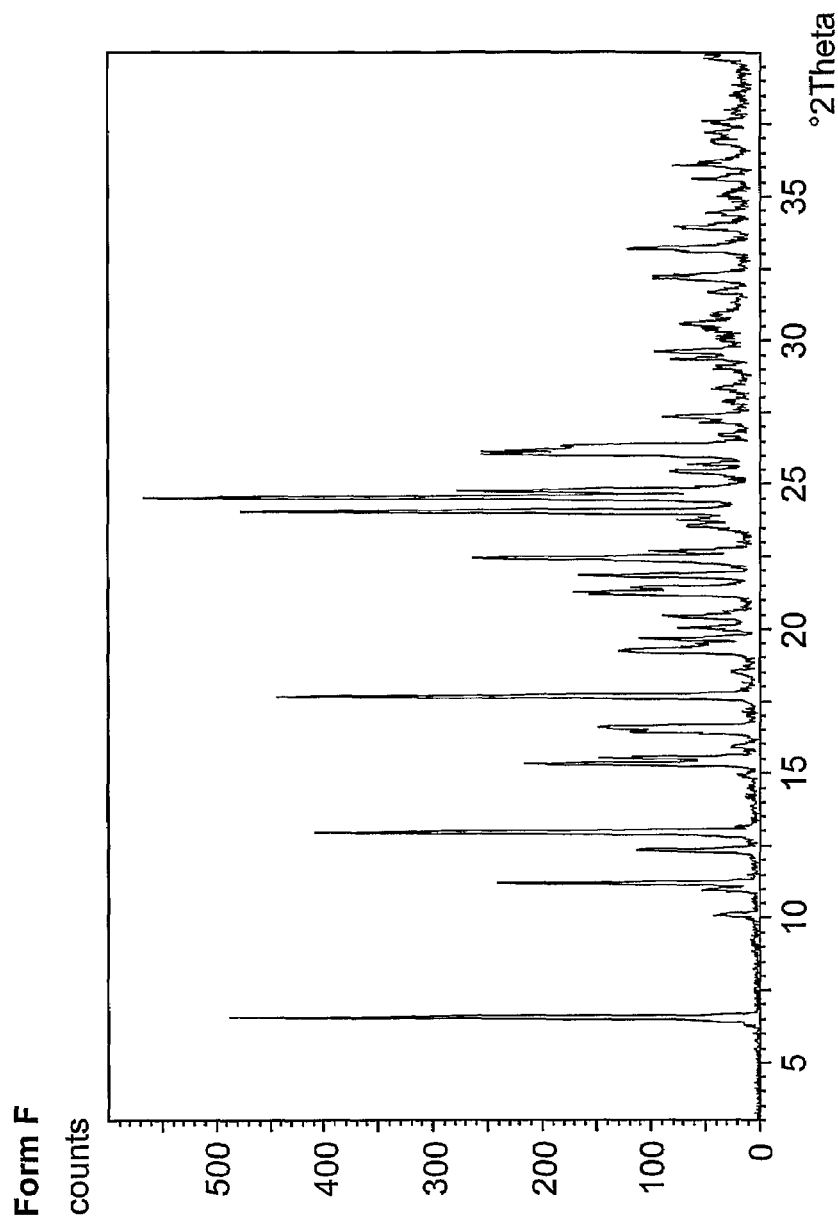
FIG. 5 is an X-ray powder diffractogram of 2,3-dimethyl-8-(2,6-dimethylbenzylamino)-N-hydroxyethyl-imidazo[1,2-a]pyridine-6-carboxamide mesylate salt form F.

2,3-dimethyl-8-(2,6-dimethylbenzylamino)-N-hydroxyethyl-imidazo[1,2-a]pyridine-6-carboxamide mesylate salt form F according to the present invention is characterized in providing an X-ray powder diffraction pattern, as in FIG. 5, exhibiting substantially the following d-values:

| Form F d-value (Å) |
|---|
| 13.5 |
| 7.9 |
| 6.9 |
| 5.8 |
| 5.0 |
| 3.96 |
| 3.70 |
| 3.63 |

It is a further aspect of the present invention to provide 2,3-dimethyl-8-(2,6-dimethylbenzylamino)-N-hydroxyethyl-imidazo[1,2-a]pyridine-6-carboxamide mesylate salt form G.

Figure 6:
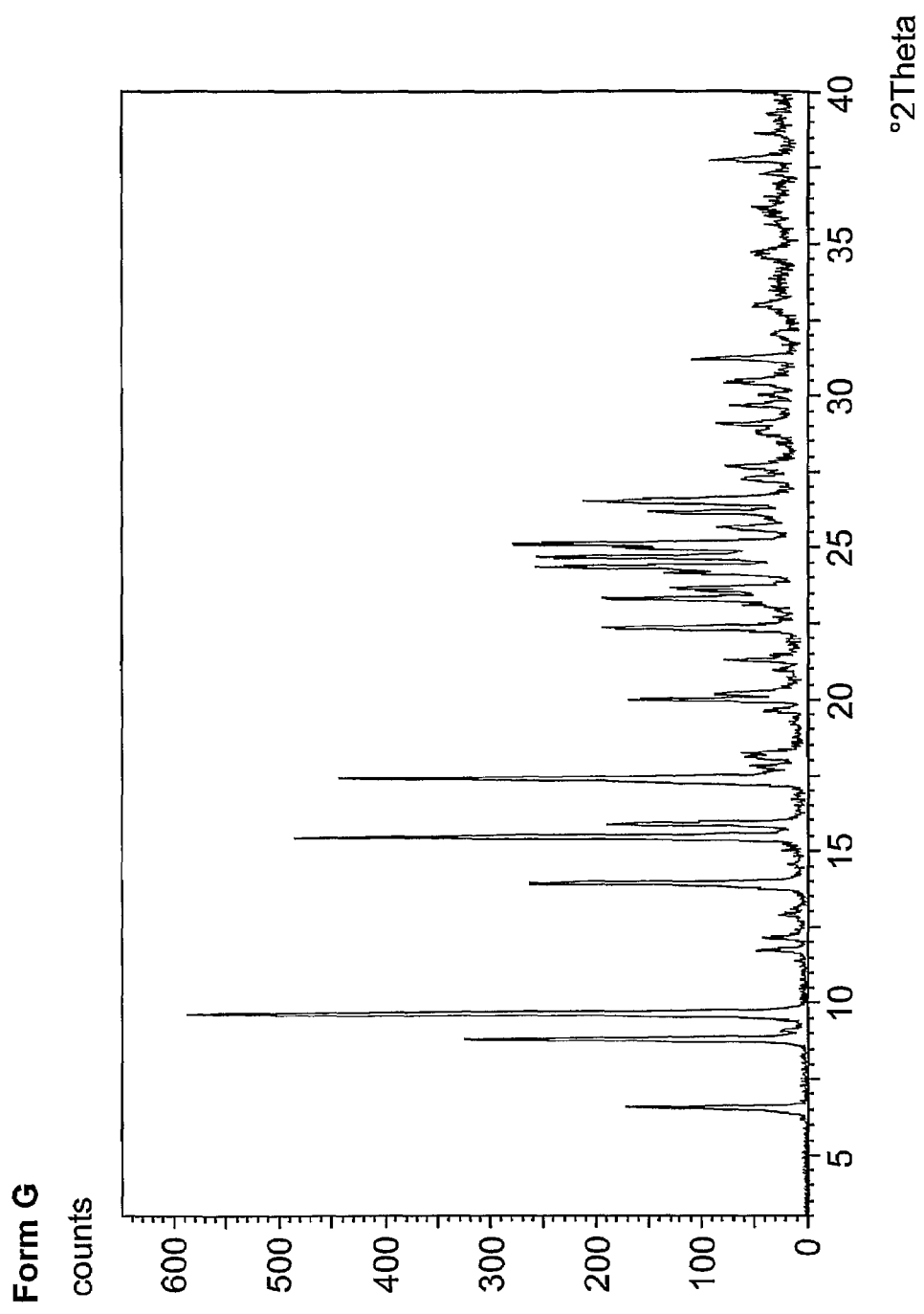
FIG. 6 is an X-ray powder diffractogram of 2,3-dimethyl-8-(2,6-dimethylbenzylamino)-N-hydroxyethyl-imidazo[1,2-a]pyridine-6-carboxamide mesylate salt form G.

2,3-dimethyl-8-(2,6-dimethylbenzylamino)-N-hydroxyethyl-imidazo[1,2-a]pyridine-6-carboxamide mesylate salt form G, according to the present invention, is characterized in providing an X-ray powder diffraction pattern, as in FIG. 6, exhibiting substantially the following d-values:

| Form G d-value (Å) |
|---|
| 13.6 |
| 10.1 |
| 9.2 |
| 6.4 |
| 5.7 |
| 5.1 |
| 3.82 |
| 3.61 |

It is a further aspect of the present invention to provide 2,3-dimethyl-8-(2,6-dimethylbenzylamino)-N-hydroxyethyl-imidazo[1,2-a]pyridine-6-carboxamide mesylate salt form H.

Figure 7:
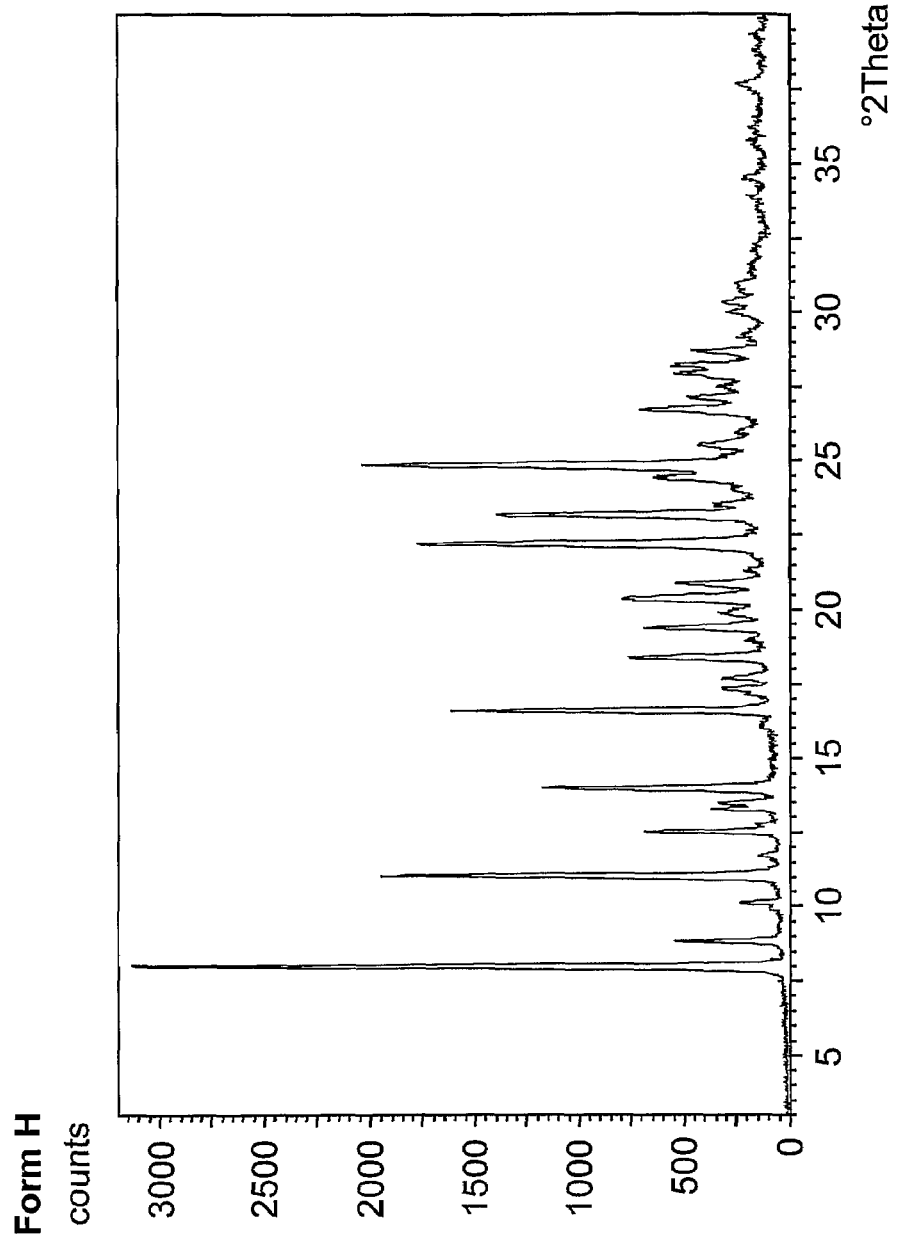
FIG. 7 is an X-ray powder diffractogram of 2,3-dimethyl-8-(2,6-dimethylbenzylamino)-N-hydroxyethyl-imidazo[1,2-a]pyridine-6-carboxamide mesylate salt form H.

2,3-dimethyl-8-(2,6-dimethylbenzylamino)-N-hydroxyethyl-imidazo[1,2-a]pyridine-6-carboxamide mesylate salt form H, according to the present invention, is characterized in providing an X-ray powder diffraction pattern, as in FIG. 7, exhibiting substantially the following d-values:

| Form H d-value (Å) |
|---|
| 11.1 |
| 8.0 |
| 7.1 |
| 6.3 |
| 5.4 |
| 4.01 |
| 3.84 |
| 3.59 |

The peaks as above, identified with d-values calculated from the Bragg formula and intensities, have been extracted from the diffractogram of the 2,3-dimethyl-8-(2,6-dimethylbenzylamino)-N-hydroxyethyl-imidazo[1,2-a]pyridine-6-carboxamide mesylate salt form A, form B, form C, form D, form E, form F, form G and form H, respectively. Only the main peaks, that are the most characteristic, significant, distinct and/or reproducible, have been tabulated, but additional peaks can be extracted, using conventional methods, from the diffractogram. The presence of these main peaks, reproducible and within the error limit (±2 on the last given decimal place), is for most circumstances sufficient to establish the presence of the said crystal modifications.

The compound of the invention 2,3-dimethyl-8-(2,6-dimethylbenzylamino)-N-hydroxyethyl-imidazo[1,2-a]pyridine-6-carboxamide mesylate salt form A, prepared according to the present invention is analyzed, characterized and differentiated from form B, form C, form D, form E, form F, form G and form H by X-ray powder diffraction, a technique which is known per se. Another suitable technique to analyze, characterize and differentiate form A from other crystal forms, such as form B is by Raman spectroscopy. The analysis, characterization and differentiation of form B, form C, form D, form E, form F, form G and form H, may be conducted in the corresponding way.

2,3-dimethyl-8-(2,6-dimethylbenzylamino)-N-hydroxyethyl-imidazo[1,2-a]pyridine-6-carboxamide mesylate salt form A and 2,3-dimethyl-8-(2,6-dimethylbenzylamino)-N-hydroxyethyl-imidazo[1,2-a]pyridine-6-carboxamide mesylate salt form B are crystalline forms exhibiting advantageous properties, such as convenient handling as well as chemical and physical stability.

It is possible to crystallize 2,3-dimethyl-8-(2,6-dimethylbenzylamino)-N-hydroxyethyl-imidazo[1,2-a]pyridine-6-carboxamide mesylate salt form A, form B, form C, form D, form E, form F, form G and form H, i.e. the crystal forms of the present invention, in one single solvent, in a mixture of solvents, or in an aqueous mixture thereof.

Suitable solvents to be used for the crystallisation are water, alcohols, such as lower alcohols, ketones, ethers, esters, haloalkanes, alkanes, halobenzenes, aliphatic nitriles and aromatic solvents, such as toluene or xylene. However, this list of solvents is not exhaustive.

The term "lower alcohol" includes herein a linear or branched $C_1$-$C_5$-alcohol, such as linear or branched $C_2$-$C_3$-alcohol. Other examples are methanol, ethanol, iso-propanol, and butanol.

Crystallization of compounds of the present invention from an appropriate solvent system, containing at least one solvent, may be achieved by attaining supersaturation in a solvent system by solvent evaporation, by temperature decrease, and/or via the addition of anti-solvent (i.e. a solvent in which the compounds of the invention are poorly soluble).

Crystallization may be initiated and/or effected with or without seeding with crystals of the appropriate crystalline compound of the invention.

Crystallization of compounds of the present invention can be achieved by in situ formation of the salt starting from pure 2,3-dimethyl-8-(2,6-dimethylbenzylamino)-N-hydroxyethyl-imidazo[1,2-a]pyridine-6-carboxamide as well as starting from 2,3-dimethyl-8-(2,6-dimethylbenzylamino)-N-hydroxyethyl-imidazo[1,2-a]pyridine-6-carboxamide mesylate salt of any form, or mixtures of any form.

Whether an anhydrate, hydrate, ansolvate or solvate crystallizes is related to the kinetics and equilibrium conditions of the respective forms at the specific conditions. Thus, as may be appreciated by the skilled person, the crystalline form that is obtained depends upon both the kinetics and the thermodynamics of the crystallization process. Under certain conditions (solvent system, temperature, pressure and concentration of compound of the invention), one crystalline form may be more stable than another (or indeed any other). However, crystalline forms that have a relatively low thermodynamic stability may be kinetically favored. Thus, in addition, kinetic factors, such as time, impurity profile, agitation, the presence or absence of seeds, etc. may also influence which form that crystallizes.

One object of the present invention is to provide processes for the preparation of 2,3-dimethyl-8-(2,6-dimethylbenzylamino)-N-hydroxyethyl-imidazo[1,2-a]pyridine-6-carboxamide mesylate salt form A, form B, form C, form D, form E, form F, form G and form H.

2,3-dimethyl-8-(2,6-dimethylbenzylamino)-N-hydroxyethyl-imidazo[1,2-a]pyridine-6-carboxamide mesylate salt form A is obtainable upon crystallization from a lower alcohol or from a mixture thereof, or from an aqueous mixture thereof. The crystallization is performed at a higher temperature, i.e. at a temperature of 40° C. or above, preferably at a temperature of 50° C. or above.

2,3-dimethyl-8-(2,6-dimethylbenzylamino)-N-hydroxyethyl-imidazo[1,2-a]pyridine-6-carboxamide mesylate salt form B is obtainable upon crystallization from a lower alcohol, or from a mixture thereof, or from an aqueous mixture thereof. The crystallization is performed at a lower temperature, i.e. at a temperature lower than 40° C., preferably at room temperature, i.e. at about 20° C. or below.

2,3-dimethyl-8-(2,6-dimethylbenzylamino)-N-hydroxyethyl-imidazo[1,2-a]pyridine-6-carboxamide mesylate salt form C, form D, and form E are obtainable upon crystallisation of form A, or of mixtures with form B, from water, or aqueous lower alcohol. Depending on the amount of water present as well as the temperature during the process, the different crystalline forms C, D and E are obtained.

2,3-dimethyl-8-(2,6-dimethylbenzylamino)-N-hydroxyethyl-imidazo[1,2-a]pyridine-6-carboxamide mesylate salt form F is obtainable upon crystallization from a mixture of water and lower alcohol, performed at lower temperature, preferably at room temperature, most preferably below room temperature.

2,3-dimethyl-8-(2,6-dimethylbenzylamino)-N-hydroxyethyl-imidazo[1,2-a]pyridine-6-carboxamide mesylate salt form G and 2,3-dimethyl-8-(2,6-dimethylbenzylamino)-N-hydroxyethyl-imidazo[1,2-a]pyridine-6-carboxamide mesylate salt form H are obtainable upon crystallization from methanol or ethanol, respectively. The crystallization of form H is performed at low temperature, preferably at room temperature, most preferably below room temperature.

In order to ensure that a particular crystalline form is prepared in the substantial absence of other crystalline forms, crystallization is preferably carried out by seeding with seed crystals of the desired crystalline form. This applies particularly to each of the specific crystalline forms which are described in the Examples. Seeds of all form are obtainable by standard procedures, for instance by repeated crystallization of a particular crystal form.

2,3-dimethyl-8-(2,6-dimethylbenzylamino)-N-hydroxyethyl-imidazo[1,2-a]pyridine-6-carboxamide mesylate salt form A and form B obtainable according to the present invention are substantially free from other crystalline and non-crystalline forms of 2,3-dimethyl-8-(2,6-dimethylbenzylamino)-N-hydroxyethyl-imidazo[1,2-a]pyridine-6-carboxamide mesylate salt. The term "substantially free from other crystalline and non-crystalline forms of 2,3-dimethyl-8-(2,6-dimethylbenzylamino)-N-hydroxyethyl-imidazo[1,2-a]pyridine-6-carboxamide mesylate salt" shall be understood to mean that the desired crystal form of 2,3-dimethyl-8-(2,6-dimethylbenzylamino)-N-hydroxyethyl-imidazo[1,2-a]pyridine-6-carboxamide mesylate salt contains less than 10%, preferably less than 5%, more preferably less than 3%, and even more preferably less than 1% of any other forms of 2,3-dimethyl-8-(2,6-dimethylbenzylamino)-N-hydroxyethyl-imidazo[1,2-a]pyridine-6-carboxamide mesylate salt.

Another aspect of the invention is mixtures of different crystalline forms of 2,3-dimethyl-8-(2,6-dimethylbenzylamino)-N-hydroxyethyl-imidazo[1,2-a]pyridine-6-carboxamide mesylate salt. The mixtures may comprise two or more of any of the crystal forms A, B, C, D, E, F, G or H. Such mixtures can also be obtained by simply mixing two or more of the crystal forms. Some special combinations of the crystal forms of the invention may be preferred, such as a combination of two or more of the crystal forms A, B and H, a combination of two or more of the crystal forms C, D and E, or a combination of crystal forms E and G.

One aspect of the invention is mixtures comprising one or more of the different crystal forms A, C, D, E, F, G or H together with form B wherein the amount of form is B, in a detectable amount of 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% (by weight). Such mixtures can also be obtained by simply mixing the different crystalline forms, i.e. mixing one or more of form A, form C, form D, form E, form F, form G and form H with form B.

One aspect of the invention is mixtures of form A and form B wherein the amount of form B is a detectable amount, 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% (by weight). Such mixtures can also be obtained by simply mixing the two forms, form A and form B.

In a further aspect, the invention relates to the compound of the invention for use in therapy, in particular for use against gastrointestinal inflammatory diseases. The invention also provides the use of the compound of the invention in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, peptic ulcer diseases, reflux esophagitis, Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding.

The compounds may also be used for effective control and treatment of heartburn and other Gastroesophageal Reflux Disease (GERD) symptoms, i.e. healing of erosive esophagitis, maintenance of erosive esophagitis, symptomatic GERD, long term management of symptomatic GERD; heartburn; regurgitation; *Helicobacter pylori* eradication; short and long-term management of acid reflux disease; treatment of sleep disturbance due to silent gastro-esophageal reflux; nausea, vomiting due to chemotherapy or post-operative conditions. They may also be used in patients in intensive care situations, to prevent, for example, acid aspiration and stress ulceration. The compounds of the invention may also be used in treatment of airway disorders such as such as bronchitis, chronic obstructive pulmonary disease (COPD), asthma, pneuminitis, pulmonary fibrosis, acid aspiration and acid asthma.

The typical daily dose of the active substance varies within a wide range and will depend on various factors such as for example the individual requirement of each patient, the route of administration and the severeness of the disease. In general, oral and parenteral dosages will be in the range of 5 to 1000 mg per day of active substance, preferably in the range of 20 to 60 mg, for example 50 mg. The compound of the invention may be administered to the patient in a continuous treatment as well as on-demand treatment, depending on the individual requirements and the disease. By the compound of the invention possibilities to improve the quality of life for the individuals suffering from gastric acid related diseases and/or gastrointestinal inflammatory diseases are given.

The compounds of the invention may be further processed before formulation into a suitable pharmaceutical formulation. For example, the crystalline form may be milled or ground into smaller particles.

According to a further aspect of the invention, there is provided a pharmaceutical formulation including one of the compounds of the invention. The pharmaceutical formulation may also include a mixture of two or more of the compounds of the invention, for example, a mixture of form A and form B of 2,3-dimethyl-8-(2,6-dimethylbenzylamino)-N-hydroxyethyl-imidazo[1,2-a]pyridine-6-carboxamide mesylate salt in admixture with at least one pharmaceutically acceptable adjuvant, diluent or carrier.

For clinical use, the compounds of the invention are formulated into pharmaceutical formulations for oral, rectal, parenteral or other modes of administration. The pharmaceutical formulation contains a compound of the invention, or a mixture of the compounds, in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1% and 95% by weight of the preparation, preferably between 0.1% and 20% by weight in preparations for parenteral use and preferably between 0.1% and 50% by weight in preparations for oral administration.

In the preparation of pharmaceutical formulations containing the crystal forms of the present invention, or a mixture thereof, in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

Soft gelatin capsules may be prepared with capsules containing the active compound of the invention, vegetable oil, fat, or other suitable vehicle for soft gelatin capsules. Hard gelatin capsules may contain granules of the crystal forms of the invention. Hard gelatin capsules may also contain the crystal forms in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the crystal forms of the invention mixed with a neutral fat base; (ii) in the form of a gelatin rectal capsule which contains the crystal forms of the invention in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent or solution just prior to administration.

Liquid preparations for oral administration may be prepared in the form of syrups or suspensions, e.g. solutions or suspensions containing from 0.1% to 20% by weight of the active ingredient and the remainder consisting of e.g. sugar or sugar alcohols and a mixture of ethanol, water, glycerol, propylene glycol and polyethylene glycol. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent or solution prior to use.

Solutions for parenteral administration may be prepared as a solution of a crystal form of the invention in a pharmaceutically acceptable solvent or solution, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent or solution extemporaneously before use.

The crystal forms according to the invention can also be used in formulations together with other active ingredients, e.g. for the treatment or prophylaxis of conditions involving infection by *Helicobacter pylori* of human gastric mucosa. Such other active ingredients may be antimicrobial agents, in particular:

β-lactam antibiotics such as amoxicillin, ampicillin, cephalothin, cefaclor or cefixime;

macrolides such as erythromycin, or clarithromycin;

tetracyclines such as tetracycline or doxycycline;

aminoglycosides such as gentamycin, kanamycin or amikacin;

quinolones such as norfloxacin, ciprofloxacin or enoxacin;

others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

The crystal forms according to the invention can also be used in formulations together with other active ingredients, e.g. for the treatment or prophylaxis of conditions involving medicament induced gastric ulcer. Such other active ingredients may be an NSAID such as naproxen, ketoprofen, ketorolac, and diclofenac, an NO-releasing NSAID, a COX-2 inhibitor or a bisphosphonate.

According to a further aspect of the invention there is provided a method of treatment of a condition where 2,3-dimethyl-8-(2,6-dimethylbenzylamino)-N-hydroxyethyl-imidazo[1,2-a]pyridine-6-carboxamide mesylate salt according to the invention is required or desired, which method includes administering a therapeutically effective amount of a crystal form of the invention to a patient in need of such treatment.

For the avoidance of doubt, "treatment" includes the therapeutic treatment, as well as the prophylaxis, of a condition.

The crystal forms of the invention have advantageous properties and/or effects. Examples of such effects are good chemical and solid state stability as well as low hygroscopicity. Thus, the crystal forms may be easily isolated crystals, they may be stable at low temperature and/or when stored over prolonged periods.

Form A can be prepared by adding, at a higher temperature, methane sulfonic acid to a mixture of 2,3-dimethyl-8-(2,6-dimethylbenzylamino)-N-hydroxyethyl-imidazo[1,2-a]pyridine-6-carboxamide, prepared according to WO 99/55706, in lower alcohol, or preferably in an aqueous mixture thereof. The solution or suspension is allowed to crystallize by precipitation. The crystallization is performed at a higher temperature, i.e. at a temperature of 40° C. or above, preferably at a temperature of 50° C. or above. Crystals of crystal form A of the invention are isolated.

Form B can be prepared by adding methane sulfonic acid to a mixture of 2,3-dimethyl-8-(2,6-dimethylbenzylamino)-N-hydroxyethyl-imidazo[1,2-a]pyridine-6-carboxamide, prepared according to WO 99/55706, in a lower alcohol, or in an aqueous mixture thereof. The crystal form B of the invention may be obtained if the reaction is performed at a lower temperature, i.e. at a temperature lower than 40° C., preferably at room temperature, i.e. at about 20° C. or below. Form B of the crystal forms of the invention, precipitates and the crystals are isolated.

Form A can also be obtained by dissolving, suspending or recrystallisation of form B of the invention in a single solvent or in a mixture of solvents, selected from water and lower alcohols, or preferably in a mixture thereof. The suspending, or dissolving, is preferably performed at a higher temperature. The crystallisation may be initiated by seeding with form A of the crystal forms of the invention.

Form B can also be obtained by dissolving, suspending or recrystallisation of form A. This is performed by suspending or dissolving form A of the crystal forms of the invention in a single solvent or in a mixture of solvents, selected from lower alcohols. The suspending and recrystallization is performed at a lower temperature. The crystallisation may be initiated by seeding with form B of the crystal forms of the invention.

Form C can be prepared by suspending either form A, form B, form D, form E, form F, form G or form H, or a mixture thereof, in water or an aqueous mixture of a lower alcohol. The crystal form C of the invention precipitates and the crystals are isolated.

Form D can be prepared by suspending either form A, form B, form C, form E, form F, form G or form H, or a mixture thereof, in water or an aqueous mixture of a lower alcohol. The crystals of form D of the invention precipitates and are isolated.

Form E can be prepared by suspending either form A, form B, form C, form D, form F, form G or form H, or a mixture thereof, in water or an aqueous mixture of a lower alcohol at lower temperature, such as at room temperature. The crystals of form E of the invention are precipitated and isolated.

Form F can be prepared by suspending either form A, form B, form C, form D, form G or form H, or a mixture thereof, in water or an aqueous mixture of a lower alcohol at lower temperature, such as at room temperature. The crystals of form F of the invention are precipitated and isolated.

Form G can be prepared by suspending either form A, form B, form C, form D, form F or form H or a mixture thereof, in methanol. The crystals of form G of the invention are precipitated and isolated.

Form H can be prepared by suspending either form A, form B, form C, form D, form F or form G, or a mixture thereof, in ethanol, at lower temperature, such as at room temperature, or below. Crystals of form H of the invention are precipitated and isolated.

The crystalline forms of 2,3-dimethyl-8-(2,6-dimethylbenzylamino)-N-hydroxyethyl-imidazo[1,2-a]pyridine-6-carboxamide mesylate salt form A, form B, and form E are anhydrates/ansolvates of the compound of the invention, form C, form D and form F are hydrates, form G and form H are solvates.

The invention is illustrated, but in no way limited, by the following examples.

EXAMPLES

General Procedures

X-ray powder diffraction (XRPD) analysis was performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray analyses were performed using a Philips X'Pert MPD and/or PANalytical X'Pert PRO MPD diffractometer.

Differential scanning calorimetry (DSC) was performed using a Perkin Elmer DSC 7 instrument, according to standard methods, for example those described in Höhne, G. W. H. et al (1996), *Differential Scanning Calorimetry*, Springer, Berlin.

Thermogravimetric analysis (TGA) was performed using a Perkin Elmer TGA 7 instrument.

DSC onset temperatures may vary in the range ±5° C. (e.g. ±2° C.), and XRPD distances may vary in the range ±2 on the last given decimal place.

Single crystal X-ray diffraction data were collected at room temperature with an Enraf-Nonius Kappa-CCD instrument equipped with graphite mono-chromatized MoK($\alpha$) radiation (2000). Accurate unit cell parameters were obtained from a real-space vector search that indexed all observed diffraction spots.

FT-Raman spectroscopy was performed using a Perkin Elmer Spectrum GX instrument.

1. Preparation of 2,3-dimethyl-8-(2,6-dimethylbenzylamino)-N-hydroxyethyl-imidazo[1,2-a]pyridine-6-carboxamide Mesylate Salt Form A

Example 1:1

100 g of 2,3-dimethyl-8-(2,6-dimethylbenzylamino)-N-hydroxyethyl-imidazo[1,2-a]pyridine-6-carboxamide was suspended in 200 ml ethanol. The suspension was heated to approximately 60° C. and a mixture of methanesulphonic acid (28.9 g) and ethanol (40 ml) was charged during approximately 80 minutes. After rinsing with ethanol (10 ml), the suspension was cooled to approximately 50° C. The crystals were isolated and washed with ethanol. The crystals were dried (dry-blowing) during 1.5 h. 102 g of 2,3-dimethyl-8-(2,6-dimethylbenzylamino)-N-hydroxyethyl-imidazo[1,2-a]pyridine-6-carboxamide mesylate salt form A was obtained.

Example 1:2

3.0 g 2,3-dimethyl-8-(2,6-dimethylbenzylamino)-N-hydroxyethyl-imidazo[1,2-a]pyridine-6-carboxamide mesylate salt form B was suspended in 6 ml water. The suspension was seeded with crystals of 2,3-dimethyl-8-(2,6-dimethylbenzylamino)-N-hydroxyethyl-imidazo[1,2-a]pyridine-6-carboxamide mesylate salt form A (0.02 g). The suspension was stirred for approximately 2 hours at 40° C. A sample was filtered off and analyzed. The sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form A.

Example 1:3

150 g 2,3-dimethyl-8-(2,6-dimethylbenzylamino)-N-hydroxyethyl-imidazo[1,2-a]pyridine-6-carboxamide mesylate salt form B was suspended in 11.25 ml water and 101 ml ethanol. The suspension was stirred at about 40° C. for 5 h. A sample was filtered off and analyzed. The sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form A.

The crystals of 2,3-dimethyl-8-(2,6-dimethylbenzylamino)-N-hydroxyethyl-imidazo[1,2-a]pyridine-6-carboxamide mesylate salt form A, according to the present invention, are characterized in providing an X-ray powder diffraction pattern, as in FIG. 1, exhibiting substantially the following d-values and intensities;

| Form A | |
|---|---|
| d-value (Å) | Relative intensity |
| 11.4 | vs |
| 9.3 | s |
| 8.0 | m |
| 7.8 | s |
| 7.4 | vw |
| 7.3 | w |
| 6.8 | w |
| 6.5 | vw |
| 6.1 | m |
| 5.8 | m |
| 5.7 | S |
| 5.0 | W |
| 4.72 | s |
| 4.66 | m |
| 4.62 | w |
| 4.49 | w |
| 4.43 | m |
| 4.35 | m |
| 4.29 | w |
| 4.10 | w |
| 3.96 | m |
| 3.92 | s |
| 3.86 | m |
| 3.68 | w |
| 3.63 | w |
| 3.56 | m |
| 3.42 | w |
| 3.18 | m |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form A. The relative intensities are less reliable and have been estimated without any divergence slit conversion.

Definition Relative Intensities:

| | | % relative intensity* |
|---|---|---|
| vs | very strong | >85% |
| s | strong | 27-85% |
| m | medium | 10-27% |
| w | weak | 5-10% |
| vw | very weak | <5% |

*the relative intensities are derived from diffractograms measured with variable slits.

It will be understood that the relative intensities of peaks may vary according to the orientation of the sample under test and on the type and setting of the instrument used so that the intensities in the X-ray powder diffraction traces included herein are illustrative and not intended to be used for absolute comparison.

Differential scanning calorimetry (DSC) on form A showed an endotherm melting with an onset of 255° C.

TGA showed a decrease in mass of ca 0.5% (20-100° C.).

Single crystals X ray diffraction analysis showed that form A crystallises as monoclinic in the space group $P2_1/c$ with four molecules in the unit cell. The unit cell dimensions were found to be:

$a=8.575(1)$ Å

$b=18.653(1)$ Å

$c=15.794(1)$ Å

$\alpha=90°$ $\beta=113.21(1)°$ $\gamma=90°$ $V=2371.0(4)$ Å$^3$.

The calculated density is $D_c=1.296(1)$ g/cm$^3$.

The crystals of 2,3-dimethyl-8-(2,6-dimethylbenzylamino)-N-hydroxyethyl-imidazo[1,2-a]pyridine-6-carboxamide mesylate salt form A, according to the present invention, are characterized in providing a Raman spectrum as in FIG. 8. Peaks from the spectrum with relative intensities above 18.6 are observed for the following Raman shifts (cm$^{-1}$):

| Raman shift (cm$^{-1}$) | Relative intensity |
|---|---|
| 2935.9 | 56.2 |
| 1671.2 | 31.8 |
| 1617.7 | 56.6 |
| 1597.2 | 35.8 |
| 1590.4 | 39.4 |
| 1533.9 | 26.3 |
| 1484.4 | 22.6 |
| 1427.1 | 100.0 |
| 1415.8 | 85.8 |
| 1392.9 | 46.7 |
| 1383.1 | 55.8 |
| 1296.2 | 20.1 |
| 1271.1 | 25.5 |
| 1258.2 | 42.0 |
| 1095.5 | 21.5 |
| 1059.7 | 20.4 |
| 1042.3 | 41.6 |
| 877.6 | 33.6 |
| 781.7 | 28.1 |
| 708.6 | 18.6 |
| 554.9 | 23.7 |
| 542.8 | 22.3 |
| 535.7 | 25.9 |
| 501.2 | 29.9 |
| 379.6 | 25.2 |
| 352.9 | 22.6 |
| 338.1 | 28.8 |
| 268.3 | 22.3 |
| 239.7 | 39.8 |
| 228.2 | 33.2 |
| 196.8 | 26.6 |

2. Preparation of 2,3-dimethyl-8-(2,6-dimethylbenzylamino)-N-hydroxyethyl-imidazo[1,2-a]pyridine-6-carboxamide Mesylate Salt Form B Example 2:1

110 g 2,3-dimethyl-8-(2,6-dimethylbenzylamino)-N-hydroxyethyl-imidazo[1,2-a]pyridine-6-carboxamide was suspended in 550 ml ethanol. 32 g methanesulphonic acid, diluted with 80 ml ethanol was charged. After rinsing with ethanol (30 ml), the suspension was stirred at room temperature until conversion to 2,3-dimethyl-8-(2,6-dimethylbenzylamino)-N-hydroxyethyl-imidazo[1,2-a]pyridine-6-carboxamide mesylate salt form B was complete. The suspension was cooled to 2° C. at −10° C./h. The crystals were isolated and vacuum dried over the night at 30° C. 133 g of 2,3-dimethyl-8-(2,6-dimethylbenzylamino)-N-hydroxyethyl-imidazo[1,2-a]pyridine-6-carboxamide mesylate salt form B was obtained.

Example 2:2

75 g 2,3-dimethyl-8-(2,6-dimethylbenzylamino)-N-hydroxyethyl-imidazo[1,2-a]pyridine-6-carboxamide was suspended in 350 ml ethanol and cooled to 10° C. 21.9 g methanesulfonic acid, diluted with 56 ml ethanol was charged. After rinsing with ethanol (44 ml), the suspension was stirred until conversion to 2,3-dimethyl-8-(2,6-dimethylbenzylamino)-N-hydroxyethyl-imidazo[1,2-a]pyridine-6-carboxamide mesylate salt form B was complete. The crystals of 2,3-dimethyl-8-(2,6-dimethylbenzylamino)-N-hydroxyethyl-imidazo[1,2-a]pyridine-6-carboxamide mesylate salt form B were isolated and vacuum dried at 30° C. over night. Yield 99%.

Example 2:3

20 g 2,3-dimethyl-8-(2,6-dimethylbenzylamino)-N-hydroxyethyl-imidazo[1,2-a]pyridine-6-carboxamide was suspended in 99.2 ml ethanol mixed with 0.8 ml water. 3.94 ml methanesulfonic acid, diluted with 15 ml ethanol was charged at 7° C. The suspension was stirred and sampled after 5 hours. The sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form B.

Example 2:4

20 g 2,3-dimethyl-8-(2,6-dimethylbenzylamino)-N-hydroxyethyl-imidazo[1,2-a]pyridine-6-carboxamide was suspended in 98.1 ml ethanol mixed with 1.9 ml water. 3.94 ml methanesulfonic acid, diluted with 15 ml ethanol, was charged at 2° C. During the charging procedure, the suspension was seeded with crystals of 2,3-dimethyl-8-(2,6-dimethylbenzylamino)-N-hydroxyethyl-imidazo[1,2-a]pyridine-6-carboxamide mesylate salt form B. The suspension was stirred and sampled after 6 hours. The sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form B.

Example 2:5

10 g 2,3-dimethyl-8-(2,6-dimethylbenzylamino)-N-hydroxyethyl-imidazo[1,2-a]pyridine-6-carboxamide was suspended in 47 ml iso-propanol. 1.97 ml methanesulfonic acid, diluted with 11 ml iso-propanol, was added at 10° C. The suspension was stirred over night and then sampled. A sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form B.

Example 2:6

2.0 g 2,3-dimethyl-8-(2,6-dimethylbenzylamino)-N-hydroxyethyl-imidazo[1,2-a]pyridine-6-carboxamide mesylate salt form A was suspended in 3 ml ethanol. The suspension was seeded with a "small amount" of 2,3-dimethyl-8-(2,6- dimethylbenzylamino)-N-hydroxyethyl-imidazo[1,2-a]pyridine-6-carboxamide mesylate salt form B. The suspension was stirred over night at room temperature. The crystals were isolated. A sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form B.

Example 2:7

2.0 g of 2,3-dimethyl-8-(2,6-dimethylbenzylamino)-N-hydroxyethyl-imidazo[1,2-a]pyridine-6-carboxamide mesylate salt form A was suspended in 3 ml of ethanol/methanol (1:1). To the suspension, 10 mg of 2,3-dimethyl-8-(2,6-dimethylbenzylamino)-N-hydroxyethyl-imidazo[1,2-a]pyridine-6-carboxamide mesylate salt form B was added. Stirring was continued for 17 h in room temperature. The solid, 2,3-dimethyl-8-(2,6-dimethylbenzylamino)-N-hydroxyethyl-imidazo[1,2-a]pyridine-6-carboxamide mesylate salt form B, was filtered off. Yield 87%.

Example 2:8

2.0 g 2,3-dimethyl-8-(2,6-dimethylbenzylamino)-N-hydroxyethyl-imidazo[1,2-a]pyridine-6-carboxamide mesylate salt form A was suspended in 3 ml ethanol/iso-propanol (1:1). To the suspension, 10 mg of 2,3-dimethyl-8-(2,6-dimethylbenzylamino)-N-hydroxyethyl-imidazo[1,2-a]pyridine-6-carboxamide mesylate salt form B was added as seeds. The suspension was stirred in 16 hours at room temperature. The solid 2,3-dimethyl-8-(2,6-dimethylbenzylamino)-N-hydroxyethyl-imidazo[1,2-a]pyridine-6-carboxamide mesylate salt form B was filtered off. Yield 93%.

Example 2:9

15 g 2,3-dimethyl-8-(2,6-dimethylbenzylamino)-N-hydroxyethyl-imidazo[1,2-a]pyridine-6-carboxamide was suspended in 70 ml ethanol. The suspension was tempered to 27° C. when a mixture of 4.3 g methanesulfonic acid and 26 ml ethanol was added during 18 minutes. The suspension was cooled to 0° C. and stirred over night. The isolated compound was verified (XRPD) to consist of 2,3-dimethyl-8-(2,6-dimethylbenzylamino)-N-hydroxyethyl-imidazo[1,2-a]pyridine-6-carboxamide mesylate salt form B. Yield: 95%.

Example 2:10

15 g 2,3-dimethyl-8-(2,6-dimethylbenzylamino)-N-hydroxyethyl-imidazo[1,2-a]pyridine-6-carboxamide was suspended in 70 ml ethanol and tempered to 37° C. when a mixture of 4.3 g methanesulfonic acid and 3 ml ethanol was added during 18 minutes. The suspension was cooled to 0° C. and stirred over night. The isolated compound was verified (XRPD) to consist of 2,3-dimethyl-8-(2,6-dimethylbenzylamino)-N-hydroxyethyl-imidazo[1,2-a]pyridine-6-carboxamide mesylate salt form B. Yield: 97%.

Example 2:11

68.8 kg 2,3-dimethyl-8-(2,6-dimethylbenzylamino)-N-hydroxyethyl-imidazo[1,2-a]pyridine-6-carboxamide was suspended in 257 kg ethanol and tempered to 30-32° C. 10% of a mixture of 20 kg methanesulfonic acid and 40 kg ethanol was added during 14 minutes and then seeded with 600 g of 2,3-dimethyl-8-(2,6-dimethylbenzylamino)-N-hydroxyethyl-imidazo[1,2-a]pyridine-6-carboxamide mesylate salt form B. The residue of the mixture of ethanol and methanesulfonic acid was added during 97 min. The suspension was sampled and was verified to consist of 2,3-dimethyl-8-(2,6-dimethylbenzylamino)-N-hydroxyethyl-imidazo[1,2-a]pyridine-6-carboxamide mesylate salt form B. The suspension was cooled to 10° C. and then the crystals were isolated. Yield: 85%.

Example 2:12

75 kg 2,3-dimethyl-8-(2,6-dimethylbenzylamino)-N-hydroxyethyl-imidazo[1,2-a]pyridine-6-carboxamide was suspended in 276 kg ethanol and tempered to 31-32° C. A mixture of 21.8 kg methanesulfonic acid and 44 kg ethanol was added during 99 minutes followed by another 34 kg of ethanol. The suspension was cooled to 110° C. and sampled after 6 h. The sample was verified to consist of 2,3-dimethyl-8-(2,6-dimethylbenzylamino)-N-hydroxyethyl-imidazo[1,2-a]pyridine-6-carboxamide mesylate salt form B. Yield: 92%.

2,3-dimethyl-8-(2,6-dimethylbenzylamino)-N-hydroxyethyl-imidazo[1,2-a]pyridine-6-carboxamide mesylate salt form B, according to the present invention, is characterized in providing an X-ray powder diffraction pattern, as in FIG. 2, exhibiting substantially the following d-values and intensities;

| Form B | |
|---|---|
| d-value (Å) | Relative intensity |
| 19.5 | w |
| 11.8 | s |
| 11.1 | m |
| 9.8 | vs |
| 8.3 | s |
| 7.8 | w |
| 6.8 | w |
| 6.5 | w |
| 6.4 | w |
| 5.9 | m |
| 5.5 | m |
| 4.96 | w |
| 4.72 | m |
| 4.52 | m |
| 4.35 | w |
| 3.89 | w |
| 3.68 | w |
| 3.26 | m |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form B. The relative intensities are less reliable and have been estimated without any divergence slit conversion.

It will be understood that the relative intensities of peaks may vary according to the orientation of the sample under test and on the type and setting of the instrument used so that the intensities in the X-ray powder diffraction traces included herein are illustrative and not intended to be used for absolute comparison.

Definition Relative Intensities:

|  |  | % relative intensity* |
|---|---|---|
| vs | very strong | >60% |
| s | strong | 30-60% |
| m | medium | 10-30% |
| w | weak | 5-10% |
| vw | very weak | <5% |

*the relative intensities are derived from diffractograms measured with variable slits.

Differential scanning calorimetry (DSC) on form B showed an exothermal event with an onset of 112° C. and an endotherm melting with an onset of 255° C.

TGA showed a decrease in mass of ca 0.2% (21-100° C.).

Single crystals X ray diffraction analysis showed that form B crystallises as trielinic in the space group P(−1) (space group No. 2) with four molecules in the unit cell. The unit cell dimensions were found to be:

$a$=8.440(1)

$b$=14.244(1)

$c$=19.898(1) Å

$\alpha$=93.03(1)°

$\beta$=99.88(1)°

$\gamma$=96.81(1)°

$V$=2333.5(4) Å$^3$.

The calculated density is $D_c$=1.317(1) g/cm$^3$.

The crystals of 2,3-dimethyl-8-(2,6-dimethylbenzylamino)-N-hydroxyethyl-imidazo[1,2-a]pyridine-6-carboxamide mesylate salt form B, according to the present invention, are characterized in providing a Raman spectrum as in FIG. 9. Peaks from the spectrum with relative intensities above 18.6 are observed for the following Raman shifts (cm$^{-1}$):

| Raman shift (cm$^{-1}$) | Relative intensity |
|---|---|
| 2937.4 | 53.5 |
| 2928.8 | 41.9 |
| 1671.4 | 33.5 |
| 1617.0 | 47.9 |
| 1590.3 | 39.1 |
| 1533.8 | 20.9 |
| 1480.7 | 20.9 |
| 1461.0 | 21.4 |
| 1426.4 | 81.9 |
| 1417.3 | 100.0 |
| 1394.4 | 50.2 |
| 1383.1 | 59.1 |
| 1357.5 | 20.9 |
| 1305.8 | 24.7 |
| 1280.3 | 19.1 |
| 1254.9 | 55.8 |
| 1163.5 | 22.8 |
| 1100.1 | 21.9 |
| 1040.8 | 50.7 |
| 964.9 | 18.6 |
| 888.2 | 34.4 |
| 871.9 | 28.4 |
| 777.4 | 31.6 |
| 751.4 | 19.1 |
| 710.3 | 18.6 |
| 553.1 | 26.0 |
| 536.1 | 26.5 |
| 501.3 | 31.2 |
| 382.3 | 22.3 |
| 353.1 | 25.6 |
| 335.5 | 32.1 |
| 285.4 | 22.8 |
| 241.1 | 41.4 |
| 198.9 | 22.3 |

3. Preparation of 2,3-dimethyl-8-(2,6-dimethylbenzylamino)-N-hydroxyethyl-imidazo[1,2-a]pyridine-6-carboxamide Mesylate Salt Form C Example 3:1

0.5 g 2,3-dimethyl-8-(2,6-dimethylbenzylamino)-N-hydroxyethyl-imidazo[1,2-a]pyridine-6-carboxamide mesylate salt (mixture of Form A and Form B) was suspended in 0.75 ml water. The suspension was stirred at 22° C. during 24 h. A sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form C.

2,3-dimethyl-8-(2,6-dimethylbenzylamino)-N-hydroxyethyl-imidazo[1,2-a]pyridine-6-carboxamide mesylate salt form C, according to the present invention, is characterized in providing an X-ray powder diffraction pattern, as in FIG. 3, exhibiting substantially the following d-values and intensities;

| Form C | |
|---|---|
| d-value (Å) | Relative intensity |
| 13.1 | vs |
| 10.7 | s |
| 10.3 | s |
| 7.1 | m |
| 6.8 | s |
| 5.8 | s |
| 5.7 | s |
| 5.5 | m |
| 5.2 | m |
| 4.88 | s |
| 4.67 | s |
| 4.43 | m |
| 4.39 | m |
| 4.20 | s |
| 4.03 | m |
| 3.95 | s |
| 3.92 | s |
| 3.83 | m |
| 3.80 | s |
| 3.76 | s |
| 3.57 | s |
| 3.51 | s |
| 3.44 | m |
| 3.35 | s |
| 3.31 | m |
| 3.17 | m |
| 2.90 | m |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form C. The relative intensities are less reliable and have been estimated without any divergence slit conversion.

Definition Relative Intensities:

|    |             | % relative intensity* |
|----|-------------|----------------------|
| vs | very strong | >85%                 |
| s  | strong      | 27-85%               |
| m  | medium      | 12-27%               |
| w  | weak        | 6-12%                |
| vw | very weak   | <6%                  |

*the relative intensities are derived from diffractograms measured with variable slits.

TGA showed a decrease in mass of ca 0.2% (21-75° C.).

4. Preparation of 2,3-dimethyl-8-(2,6-dimethylbenzylamino)-N-hydroxyethyl-imidazo[1,2-a]pyridine-6-carboxamide Mesylate Salt Form D Example 4:1

A suspension of crystals of 2,3-dimethyl-8-(2,6-dimethylbenzylamino)-N-hydroxyethyl-imidazo[1,2-a]pyridine-6-carboxamide mesylate salt form C was isolated, the crystals were dried shortly in open-air. A sample was analysed (XRPD) and was verified to consist of crystals of 2,3-dimethyl-8-(2,6-dimethylbenzylamino)-N-hydroxyethyl-imidazo[1,2-a]pyridine-6-carboxamide mesylate salt form D.

2,3-dimethyl-8-(2,6-dimethylbenzylamino)-N-hydroxyethyl-imidazo[1,2-a]pyridine-6-carboxamide mesylate salt form D, according to the present invention, is characterized in providing an X-ray powder diffraction pattern exhibiting substantially the following d-values and intensities;

| Form D            |                    |
|-------------------|--------------------|
| d-value (Å)       | Relative intensity |
| 13.8              | s                  |
| 9.1               | s                  |
| 7.2               | w                  |
| 6.9               | s                  |
| 6.4               | s                  |
| 5.9               | m                  |
| 5.8               | m                  |
| 5.6               | w                  |
| 5.1               | m                  |
| 5.0               | w                  |
| 4.85              | w                  |
| 4.62              | m                  |
| 4.43              | w                  |
| 4.19              | m                  |
| 3.92              | m                  |
| 3.87              | m                  |
| 3.71              | w                  |
| 3.59              | m                  |
| 3.55              | m                  |
| 3.39              | w                  |
| 3.13              | w                  |
| 2.64              | w                  |
| 2.38              | m                  |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form D. The relative intensities are less reliable and have been estimated without any divergence slit conversion.

Definition Relative Intensities:

|    |           | % relative intensity* |
|----|-----------|----------------------|
| s  | strong    | >60%                 |
| m  | medium    | 17-60%               |
| w  | weak      | 7-17%                |
| vw | very weak | <7%                  |

*the relative intensities are derived from diffractograms measured with variable slits.

Single crystals X ray diffraction analysis showed that form D crystallises as triclinic in the space group P(−1) (space group No. 2) with four molecules in the unit cell. The unit cell dimensions were found to be:

$a=8.613(1)$ Å

$b=15.908(1)$ Å

$c=19.401(1)$ Å

$\alpha=70.27(1)°$ $\beta=89.14(1)°$ $\gamma=74.86(1)°$ $V=2407.5$ Å$^3$.

The calculated density is $D_c=1.301(1)$ g/cm$^3$.

5. Preparation of 2,3-dimethyl-8-(2,6-dimethylbenzylamino)-N-hydroxyethyl-imidazo[1,2-a]pyridine-6-carboxamide Mesylate Salt Form E Example 5:1

A suspension of crystals of 2,3-dimethyl-8-(2,6-dimethylbenzylamino)-N-hydroxyethyl-imidazo[1,2-a]pyridine-6-carboxamide mesylate salt form C was isolated at room temperature. The crystals were dried at 40° C. by vacuum over the night. The crystals were analysed (XRPD) and verified to consist of crystals of 2,3-dimethyl-8-(2,6-dimethylbenzylamino)-N-hydroxyethyl-imidazo[1,2-a]pyridine-6-carboxamide mesylate salt form E.

2,3-dimethyl-8-(2,6-dimethylbenzylamino)-N-hydroxyethyl-imidazo[1,2-a]pyridine-6-carboxamide mesylate salt form E, according to the present invention, is characterized in providing an X-ray powder diffraction pattern, as in FIG. 4, exhibiting substantially the following d-values and intensities;

| Form E       |                    |
|--------------|--------------------|
| d-value (Å)  | Relative intensity |
| 12.5         | m                  |
| 10.1         | s                  |
| 9.5          | vs                 |
| 6.8          | w                  |
| 6.2          | m                  |
| 6.1          | s                  |
| 5.5          | m                  |

-continued

Form E

| d-value (Å) | Relative intensity |
|---|---|
| 5.1 | m |
| 4.61 | m |
| 4.41 | w |
| 4.14 | m |
| 3.88 | m |
| 3.82 | m |
| 3.71 | m |
| 3.41 | m |
| 2.98 | m |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form E. The relative intensities are less reliable and have been estimated without any divergence slit conversion.

Definition Relative Intensities:

| | | % relative intensity* |
|---|---|---|
| vs | very strong | >70% |
| s | strong | 33-70% |
| m | medium | 10-33% |
| w | weak | 5-10% |
| vw | very weak | <5% |

*the relative intensities are derived from diffractograms measured with variable slits.

TGA showed a decrease in mass of ca 0.2% (21-200° C.).

6. Preparation of 2,3-dimethyl-8-(2,6-dimethylbenzylamino)-N-hydroxyethyl-imidazo[2-a]pyridine-6-carboxamide Mesylate Salt Form F Example 6:1

3.0 g of moist 2,3-dimethyl-8-(2,6-dimethylbenzylamino)-N-hydroxyethyl-imidazo[1,2-a]pyridine-6-carboxamide mesylate salt form A was suspended in 0.68 ml water and 3.85 ml ethanol. The suspension was stirred at −10° C. for 4 days. A sample was filtered off and analyzed. The sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form F.

Example 6:2

3.0 g of 2,3-dimethyl-8-(2,6-dimethylbenzylamino)-N-hydroxyethyl-imidazo[1,2-a]pyridine-6-carboxamide mesylate salt form A was suspended in 4.5 ml of a mixture of ethanol and water (1:1). The suspension was stirred at room temperature during 4 days. A sample was verified (XRPD) to consist of crystals of 2,3-dimethyl-8-(2,6-dimethylbenzylamino)-N-hydroxyethyl-imidazo[1,2-a]pyridine-6-carboxamide mesylate salt form F.

2,3-dimethyl-8-(2,6-dimethylbenzylamino)-N-hydroxyethyl-imidazo[1,2-a]pyridine-6-carboxamide mesylate salt form F according to the present invention, is characterized in providing an X-ray powder diffraction pattern, as in FIG. 5, exhibiting substantially the following d-values and intensities:

Form F

| d-value (Å) | Relative intensity |
|---|---|
| 13.5 | s |
| 8.1 | w |
| 7.9 | m |
| 7.2 | m |
| 6.9 | s |
| 5.8 | m |
| 5.7 | m |
| 5.4 | m |
| 5.0 | s |
| 4.62 | m |
| 4.52 | m |
| 4.44 | w |
| 4.35 | w |
| 4.18 | m |
| 4.15 | m |
| 4.07 | m |
| 3.96 | m |
| 3.92 | m |
| 3.78 | w |
| 3.70 | s |
| 3.63 | s |
| 3.60 | m |
| 3.50 | w |
| 3.26 | w |
| 3.05 | w |
| 3.02 | w |
| 2.78 | w |
| 2.70 | m |
| 2.65 | w |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form F. The relative intensities are less reliable and have been estimated without any divergence slit conversion.

Definition Relative Intensities:

| | | % relative intensity* |
|---|---|---|
| s | strong | >60% |
| m | medium | 17-60% |
| w | weak | 7-17% |
| vw | very weak | <7% |

*the relative intensities are derived from diffractograms measured with variable slits.

TGA showed a decrease in mass of ca 3.4% (25-75° C.).

7. Preparation of 2,3-dimethyl-8-(2,6-dimethylbenzylamino)-N-hydroxyethyl-imidazo[1,2-a]pyridine-6-carboxamide Mesylate Salt Form G Example 7:1

0.5 g of 2,3-dimethyl-8-(2,6-dimethylbenzylamino)-N-hydroxyethyl-imidazo[1,2-a]pyridine-6-carboxamide mesylate salt, mixture of form A and form B, was suspended in 0.75 ml methanol. The suspension was added to a vial and the system was closed. The suspension was stirred over night at room temperature. A sample was filtered off and analyzed. The sample was verified (XRPD) to consist of crystals of 2,3-dimethyl-8-(2,6-dimethylbenzylamino)-N-hydroxy-ethyl-imidazo[1,2-a]pyridine-6-carboxamide mesylate salt form G.

2,3-dimethyl-8-(2,6-dimethylbenzylamino)-N-hydroxy-ethyl-imidazo[1,2-a]pyridine-6-carboxamide mesylate salt form G, according to the present invention, is characterized in providing an X-ray powder diffraction pattern, as in FIG. 6, exhibiting substantially the following d-values and intensities;

| Form G | |
|---|---|
| d-value (Å) | Relative intensity |
| 13.6 | m |
| 10.1 | s |
| 9.2 | s |
| 7.6 | w |
| 7.3 | w |
| 6.4 | m |
| 5.7 | s |
| 5.6 | m |
| 5.1 | s |
| 4.45 | m |
| 4.41 | w |
| 4.18 | w |
| 3.98 | m |
| 3.82 | m |
| 3.76 | w |
| 3.66 | m |
| 3.61 | m |
| 3.55 | m |
| 3.48 | w |
| 3.41 | m |
| 3.36 | m |
| 3.23 | w |
| 3.08 | w |
| 2.87 | w |
| 2.38 | w |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form G. The relative intensities are less reliable and have been estimated without any divergence slit conversion.

Definition Relative Intensities:

| | | % relative intensity* |
|---|---|---|
| s | strong | >50% |
| m | medium | 22-50% |
| w | weak | 6-22% |
| vw | very weak | <6% |

*the relative intensities are derived from diffractograms measured with variable slits.

TGA showed a decrease in mass of ca 18.6% (23-81° C.), and of ca 5.2% (81-100° C.).

8. Preparation of 2,3-dimethyl-8-(2,6-dimethylbenzylamino)-N-hydroxyethyl-imidazo[1,2-a]pyridine-6-carboxamide Mesylate Salt Form H Example 8:1

40 g 2,3-dimethyl-8-(2,6-dimethylbenzylamino)-N-hydroxyethyl-imidazo[1,2-a]pyridine-6-carboxamide was suspended in 187 ml ethanol and cooled to 10° C. 11.7 g methanesulfonic acid, diluted with 40 ml ethanol was charged. After rinsing with ethanol (13 ml) the suspension was stirred for five hours. The crystals were collected in a filter, washed and dried in vacuum at 30° C. for 64 hours. The crystals were verified (XRPD) to consist of 2,3-dimethyl-8-(2,6-dimethylbenzylamino)-N-hydroxyethyl-imidazo[1,2-a]pyridine-6-carboxamide mesylate salt form H.

2,3-dimethyl-8-(2,6-dimethylbenzylamino)-N-hydroxy-ethyl-imidazo[1,2-a]pyridine-6-carboxamide mesylate salt form H, according to the present invention, is characterized in providing an X-ray powder diffraction pattern, as in FIG. 7, exhibiting substantially the following d-values and intensities:

| Form H | |
|---|---|
| d-value (Å) | Relative intensity |
| 11.1 | vs |
| 10.1 | m |
| 8.8 | w |
| 8.0 | s |
| 7.1 | m |
| 6.7 | w |
| 6.6 | w |
| 6.3 | m |
| 5.4 | s |
| 4.84 | m |
| 4.59 | m |
| 4.37 | m |
| 4.27 | w |
| 4.01 | s |
| 3.84 | s |
| 3.65 | m |
| 3.59 | s |
| 3.34 | m |
| 3.20 | w |
| 3.17 | w |
| 3.11 | w |

The peaks, identified with d-values calculated from the Bragg formula and intensities, have been extracted from the diffractogram of 2,3-dimethyl-8-(2,6-dimethylbenzylamino)-N-hydroxyethyl-imidazo[1,2-a]pyridine-6-carboxamide mesylate salt form H. The relative intensities are less reliable and have been estimated without any divergence slit conversion.

Definition Relative Intensities:

| | | % relative intensity* |
|---|---|---|
| vs | very strong | >85% |
| s | strong | 37-85% |
| m | medium | 14-37% |
| w | weak | 6-14% |
| vw | very weak | <6% |

*the relative intensities are derived from diffractograms measured with variable slits.

TGA showed a decrease in mass of ca 5.4% (22-150° C.).

The invention claimed is:
1. 2,3-Dimethyl-8-(2,6-dimethylbenzylamino)-N-hydroxyethyl-imidazo-[1,2-a]pyridine-6-carboxamide mesylate salt and crystalline forms thereof.
2. The compound according to claim 1, wherein the crystalline form is 2,3-dimethyl-8-(2,6-dimethylbenzylamino)-

N-hydroxyethyl-imidazo-[1,2-a]pyridine-6-carboxamide mesylate salt form A, characterized by a triclinic unit cell with parameters:

a=8.6 Å, b=18.7 Å, c=15.8 Å, α=90°, β=113°, γ=90°.

3. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form A, characterized by an X-ray powder diffraction pattern exhibiting substantially the following d-values:

| Form A d-value (Å) |
|---|
| 11.4 |
| 9.3 |
| 7.8 |
| 5.7 |
| 4.72 |
| 4.35 |
| 3.92 |
| 3.18. |

4. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form A, characterized by a Raman Spectrum exhibiting substantially the following relative intensities above 18.6:

| Raman shift (cm$^{-1}$) | Relative intensity |
|---|---|
| 2935.9 | 56.2 |
| 1671.2 | 31.8 |
| 1617.7 | 56.6 |
| 1597.2 | 35.8 |
| 1590.4 | 39.4 |
| 1533.9 | 26.3 |
| 1484.4 | 22.6 |
| 1427.1 | 100.0 |
| 1415.8 | 85.8 |
| 1392.9 | 46.7 |
| 1383.1 | 55.8 |
| 1296.2 | 20.1 |
| 1271.1 | 25.5 |
| 1258.2 | 42.0 |
| 1095.5 | 21.5 |
| 1059.7 | 20.4 |
| 1042.3 | 41.6 |
| 877.6 | 33.6 |
| 781.7 | 28.1 |
| 708.6 | 18.6 |
| 554.9 | 23.7 |
| 542.8 | 22.3 |
| 535.7 | 25.9 |
| 501.2 | 29.9 |
| 379.6 | 25.2 |
| 352.9 | 22.6 |
| 338.1 | 28.8 |
| 268.3 | 22.3 |
| 239.7 | 39.8 |
| 228.2 | 33.2 |
| 196.8 | 26.6. |

5. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form B, characterized by a triclinic unit cell with parameters:

a=8.4 Å, b=14.2 Å, c=19.9 Å, α=93°, β=100°, γ=97°.

6. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form B, characterized by an X-ray powder diffraction pattern exhibiting substantially the following d-values:

| Form B d-value (Å) |
|---|
| 11.8 |
| 11.1 |
| 9.8 |
| 8.3 |
| 5.9 |
| 5.5 |
| 4.72 |
| 4.52. |

7. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form B, characterized by a Raman Spectrum exhibiting substantially the following relative intensities above 18.6:

| Raman shift (cm$^{-1}$) | Relative intensity |
|---|---|
| 2937.4 | 53.5 |
| 2928.8 | 41.9 |
| 1671.4 | 33.5 |
| 1617.0 | 47.9 |
| 1590.3 | 39.1 |
| 1533.8 | 20.9 |
| 1480.7 | 20.9 |
| 1461.0 | 21.4 |
| 1426.4 | 81.9 |
| 1417.3 | 100.0 |
| 1394.4 | 50.2 |
| 1383.1 | 59.1 |
| 1357.5 | 20.9 |
| 1305.8 | 24.7 |
| 1280.3 | 19.1 |
| 1254.9 | 55.8 |
| 1163.5 | 22.8 |
| 1100.1 | 21.9 |
| 1040.8 | 50.7 |
| 964.9 | 18.6 |
| 888.2 | 34.4 |
| 871.9 | 28.4 |
| 777.4 | 31.6 |
| 751.4 | 19.1 |
| 710.3 | 18.6 |
| 553.1 | 26.0 |
| 536.1 | 26.5 |
| 501.3 | 31.2 |
| 382.3 | 22.3 |
| 353.1 | 25.6 |
| 335.5 | 32.1 |
| 285.4 | 22.8 |
| 241.1 | 41.4 |
| 198.9 | 22.3. |

8. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form C, characterized by an X-ray powder diffraction pattern exhibiting substantially the following d-values:

| Form C d-value (Å) |
|---|
| 13.1 |
| 10.7 |
| 6.8 |
| 5.7 |
| 4.88 |
| 4.39 |
| 3.57 |
| 3.51. |

9. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form D, characterized by an X-ray powder diffraction pattern exhibiting substantially the following d-values:

| Form D d-value (Å) |
|---|
| 13.8 |
| 9.1 |
| 6.9 |
| 6.4 |
| 5.1 |
| 4.62 |
| 3.55 |
| 2.38. |

10. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form D, characterized by a triclinic unit cell with parameters:

a=8.6 Å, b=15.9 Å, c=19.4 Å, α=70°, β=89°, γ=75°.

11. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form E, characterized by an X-ray powder diffraction pattern exhibiting substantially the following d-values:

| Form E d-value (Å) |
|---|
| 12.5 |
| 10.1 |
| 9.5 |
| 6.1 |
| 5.1 |
| 4.61 |
| 3.88 |
| 3.71. |

12. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form F, characterized by an X-ray powder diffraction pattern exhibiting substantially the following d-values:

| Form F d-value (Å) |
|---|
| 13.5 |
| 7.9 |
| 6.9 |
| 5.8 |
| 5.0 |
| 3.96 |
| 3.70 |
| 3.63. |

13. The compound according to claim 1, wherein the crystalline form is 2,3-dimethyl-8-(2,6-dimethylbenzylamino)-N-hydroxyethyl-imidazo-[1,2-a]pyridine-6-carboxamide mesylate salt form G, characterized by an X-ray powder diffraction pattern exhibiting substantially the following d-values:

| Form G d-value (Å) |
|---|
| 13.6 |
| 10.1 |
| 9.2 |
| 6.4 |
| 5.7 |
| 5.1 |
| 3.82 |
| 3.61. |

14. The compound according to claim 1 wherein the crystalline form is 2,3-dimethyl-8-(2,6-dimethylbenzylamino)-N-hydroxyethyl-imidazo-[1,2-a]pyridine-6-carboxamide mesylate salt form H, characterized by an X-ray powder diffraction pattern exhibiting substantially the following d-values:

| Form H d-value (Å) |
|---|
| 11.1 |
| 8.0 |
| 7.1 |
| 6.3 |
| 5.4 |
| 4.01 |
| 3.84 |
| 3.59. |

15. 2,3-Dimethyl-8-(2,6-dimethylbenzylamino)-N-hydroxyethyl-imidazo[1,2-a]pyridine-6-carboxamide mesylate salt comprising a mixture of two or more of the crystalline forms of 2,3-dimethyl-8-(2,6-dimethylbenzylamino)-N-hydroxyethyl-imidazo[1,2-a]pyridine-6-carboxamide mesylate salt according to any one of claims 2 to 14.

16. 2,3-Dimethyl-8-(2,6-dimethylbenzylamino)-N-hydroxyethyl-imidazo[1,2-a]pyridine-6-carboxamide mesylate salt comprising a mixture of form A and form B.

17. 2,3-Dimethyl-8-(2,6-dimethylbenzylamino)-N-hydroxyethyl-imidazo[1,2-a]pyridine-6-carboxamide mesylate salt comprising a mixture of two or more crystalline forms of the compound selected from the group consisting of form A, form B and form H.

18. A process for obtaining form A according to any one of claims 2 to 4 comprising the steps of:
   a) dissolving or suspending 2,3-dimethyl-8-(2,6-dimethylbenzylamino)-N-hydroxyethyl-imidazo[1,2-a]pyridine-6-carboxamide in a suitable solvent;
   b) adding methanesulfonic acid at a temperature of 40° C. or greater;
   c) allowing the solution or suspension to crystallize; and
   d) isolating the form A thus obtained.

19. A process for obtaining form B according to any one of claims 5 to 7 comprising the steps of:
   a) dissolving or suspending 2,3-dimethyl-8-(2,6-dimethylbenzylamino)-N-hydroxyethyl-imidazo[1,2-a]pyridine-6-carboxamide in a suitable solvent;
   b) adding methanesulfonic acid at a temperature lower than 40° C.;
   c) allowing the solution or suspension to crystallize; and
   d) isolating the form B thus obtained.

20. A process for obtaining form A according to any one of claims 2 to 4 comprising the steps of:
   a) dissolving or suspending any form of 2,3-dimethyl-8-(2,6-dimethylbenzylamino)-N-hydroxyethyl-imidazo[1,2-a]pyridine-6-carboxamide mesylate salt in a suitable solvent;
   b) allowing the solution or suspension to crystallize at a temperature of 40° C. or greater, optionally using form A to induce crystallization; and
   c) isolating the form A thus obtained.

21. A process for obtaining form B according to any one of claims 5 to 7 comprising the steps of:
   a) dissolving or suspending any form of 2,3-dimethyl-8-(2,6-dimethylbenzylamino)-N-hydroxyethyl-imidazo[1,2-a]pyridine-6-carboxamide mesylate salt in a suitable solvent;
   b) allowing the solution or suspension to crystallize at a temperature lower than 40° C., optionally using form B to induce crystallization; and
   c) isolating the form B thus obtained.

22. The process according to claim 20, wherein form B of 2,3-dimethyl-8-(2,6-dimethylbenzylamino)-N-hydroxyethyl-imidazo[1,2-a]pyridine-6-carboxamide mesylate salt is dissolved or suspended in accordance with step a).

23. The process according to claim 21, wherein form A of 2,3-dimethyl-8-(2,6-dimethylbenzylamino)-N-hydroxyethyl-imidazo[1,2-a]pyridine-6-carboxamide mesylate salt is dissolved or suspended in accordance with step a).

24. The process according to claim 18 or 19, wherein seeds are added to the solution or suspension to induce crystallization.

25. 2,3-Dimethyl-8-(2,6-dimethylbenzylamino)-N-hydroxyethyl-imidazo[1,2-a]pyridine-6-carboxamide mesylate salt form A prepared according to any one of claims 18, 20, 22 or 24.

26. A pharmaceutical formulation comprising at least one of the crystalline forms of 2,3-dimethyl-8-(2,6-dimethylbenzylamino)-N-hydroxyethyl-imidazo-[1,2-a]pyridine-6-carboxamide mesylate salt according to any one of claims 1 to 14 in admixture with at least one pharmaceutically acceptable excipient.

27. A method for inhibiting gastric acid secretion, the method comprising the administration of a therapeutically effective amount of 2,3-dimethyl-8-(2,6-dimethyl-benzylamino)-N-hydroxyethyl-imidazo [1,2-a]pyridine-6-carboxamide mesylate salt according to any one of claims 1 to 14 to a patient in need thereof.

28. 2,3-Dimethyl-8-(2,6-dimethylbenzylamino)-N-hydroxyethyl-imidazo[1,2-a]pyridine-6-carboxamide mesylate salt form B prepared according to any one of claims 19, 21, 23, or 24.

* * * * *